United States Patent [19]
Tanzer et al.

[11] Patent Number: 5,782,819
[45] Date of Patent: Jul. 21, 1998

[54] ARTICLE WITH STAY-IN-PLACE FEATURE

[75] Inventors: Richard Warren Tanzer; Christopher Peter Olson, both of Neenah; Thomas Walter Odorzynski, Green Bay; Paul John Serbiak, Appleton, all of Wis.

[73] Assignee: Kimberly-Clark Worldwide, Inc., Neenah, Wis.

[21] Appl. No.: 731,676

[22] Filed: Oct. 17, 1996

[51] Int. Cl.⁶ ............................................. A61F 13/15
[52] U.S. Cl. ................... 604/385.1; 604/387; 604/396; 2/337
[58] Field of Search ................. 604/385.1, 385.2, 604/386, 387, 389–396; 2/337

[56] References Cited

U.S. PATENT DOCUMENTS

| | | | |
|---|---|---|---|
| 1,046,798 | 12/1912 | Jones | 2/337 |
| 1,817,991 | 8/1931 | Langrock | 2/337 |
| 1,933,391 | 10/1933 | Reeves | 2/337 |
| 3,052,890 | 9/1962 | Miller | 2/337 |
| 3,069,691 | 12/1962 | Svojse | 2/337 |
| 3,076,201 | 2/1963 | Winter | 2/337 |
| 3,423,764 | 1/1969 | Causling | 2/337 |
| 3,901,236 | 8/1975 | Assarsson et al. | |
| 4,076,663 | 2/1978 | Masuda et al. | |
| 4,286,082 | 8/1981 | Tsubakimoto et al. | |
| 4,663,220 | 5/1987 | Wisneski et al. | |
| 4,699,823 | 10/1987 | Kellenberger et al. | |
| 4,704,116 | 11/1987 | Enloe | |
| 4,753,646 | 6/1988 | Enloe | |
| 4,916,005 | 4/1990 | Lippert et al. | |
| 4,938,753 | 7/1990 | Van Gompel et al. | 604/385.2 |
| 4,940,464 | 7/1990 | Van Gompel et al. | 604/396 |
| 5,019,073 | 5/1991 | Roessler et al. | 604/391 |
| 5,100,399 | 3/1992 | Jenson et al. | 604/391 |
| 5,112,326 | 5/1992 | Quadrini | 604/391 |
| 5,226,992 | 7/1993 | Morman | 156/62.4 |
| 5,399,219 | 3/1995 | Roessler et al. | 156/259 |

FOREIGN PATENT DOCUMENTS

| | | |
|---|---|---|
| 0 131 490 A1 | 1/1985 | European Pat. Off. . |
| 0 217 032 A3 | 4/1987 | European Pat. Off. . |
| 2 716 900 | 9/1995 | France . |
| 3 445 620 A1 | 12/1984 | Germany . |
| 1 282 421 | 7/1972 | United Kingdom . |
| 1 284 860 | 8/1972 | United Kingdom . |
| 3003969 | 3/1993 | WIPO ............... 604/385.1 |
| WO 95/22306 | 8/1995 | WIPO . |

OTHER PUBLICATIONS

ASTM D 1894—93, Standard Test Method for Static and Kinetic Coefficients of Friction of Plastic Film and Sheeting, pp. 455–459.

*Primary Examiner*—Mark O. Polutta
*Attorney, Agent, or Firm*—Paul Yee

[57] ABSTRACT

An article (20) has a front waistband section (38), a back waistband section (40), an intermediate section (42) interconnecting the front and back waistband sections, a longitudinal direction (86), a cross-direction (88) and a laterally extending line (100) which is longitudinally centered in the article (20). At least a first fit panel (36) is connected to an inside surface (66) of at least one of the waistband sections (38, 40), and the fit panel has a direction-dependent coefficient of friction value along a basis line (54) of the fit panel. A first coefficient of friction value is exhibited when sliding on the fit panel along the basis line in a first, inward basis direction (62) generally toward the lateral line and a different second coefficient of friction value is exhibited when sliding on the fit panel along the basis line in a second, outward basis direction (64) which is opposite the first basis direction (62).

38 Claims, 9 Drawing Sheets

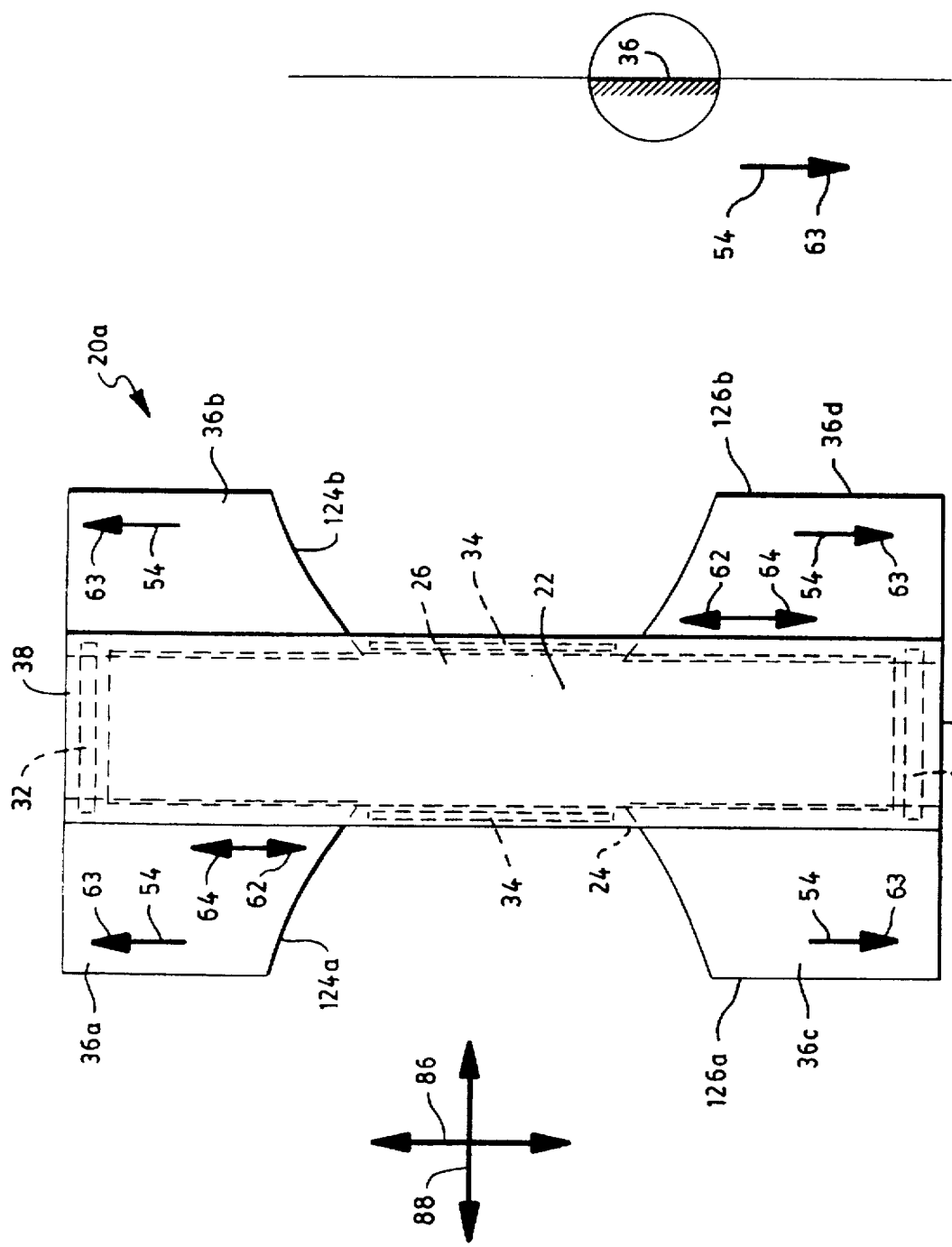

5,782,819

ARTICLE WITH STAY-IN-PLACE FEATURE

FIELD OF THE INVENTION

The present invention relates to garment articles. More particularly, the present invention relates to absorbent articles, especially disposable absorbent articles, which have improved fit and performance.

BACKGROUND OF THE INVENTION

Conventional garment articles, such as disposable diapers and other disposable absorbent articles, have typically employed adhesive or mechanical fasteners which attach appointed waistband sections of the articles around a wearer. In addition, various configurations of waist elastics, leg elastics, elasticized liners, and elasticized outcovers have been employed on garment articles to help produce and maintain the fit of the articles about the body contours of the wearer.

Conventional garment articles, such as those described above, have not provided desired levels of reliable fit, and have been susceptible to excessive sagging and drooping during the period of wearing. The garment structures have not adequately maintained the desired levels of fit and comfort, and where the garments are configured as absorbent articles, the articles have been susceptible to excessive leakage of liquids and other waste materials. As a result, there has been a continued need for improved garments having more consistent fit and greater resistance to sagging and drooping.

BRIEF DESCRIPTION OF THE INVENTION

Generally stated, the present invention provides a distinctive article which includes a a front waistband section, a back waistband section, an intermediate section interconnecting the front and back waistband sections, a longitudinal direction, a cross-direction and a laterally extending line which is longitudinally centered in the article. At least a first fit panel is connected to an inside surface of at least one of the waistband sections, and the fit panel has a direction-dependent coefficient of friction value along a basis line of the fit panel. A first coefficient of friction value is exhibited when sliding on the fit panel along the basis line in a first, inward basis direction generally toward the lateral line and a different, second coefficient of friction value is exhibited when sliding on the fit panel along the basis line in a second, outward basis direction which is opposite the first basis direction.

In its various aspects, the article of present invention can provide more reliable and more consistent fit about the wearer with greater resistance to sagging and drooping. The desired fit can be maintained even when the wearer is highly active. Where the garment is an absorbent article the improved resistance to drooping can reduce gapping between the garment and wearer, and can reduce the leakage of liquid or semi-liquid waste materials.

BRIEF DESCRIPTION OF THE DRAWINGS

The present invention will be more fully understood and further advantages will become apparent when reference is made to the following detailed description of the invention and the drawings, in which:

FIG. 8 representatively shows a top view of a partially assembled, garment article of the invention where a plurality of fit panel portions are located on the body-facing surfaces of a plurality of side members which are appointed for joining to form a three-dimensional garment;

FIG. 9 representatively shows a schematic, cross-sectional view of a fabric having a majority of its fibers slanted along a substantially common direction.

DETAILED DESCRIPTION OF THE INVENTION

The various aspects and embodiments of the invention will be described in the context of a disposable absorbent article, such as a disposable diaper. It is, however, readily apparent that the present invention could also be employed with other articles, such as caps, gowns, shoe covers, feminine care articles, incontinence garments and the like, which may be configured to be disposable. Typically, disposable articles, such as disposable garments, are intended for limited use and are not intended to be laundered or otherwise cleaned for reuse. A disposable diaper, for example, is discarded after it has become soiled by the wearer. In the context of the present invention, a mechanical fastening system is a system which includes cooperating components which mechanically inter-engage to provide a desired securement.

Figure 1:
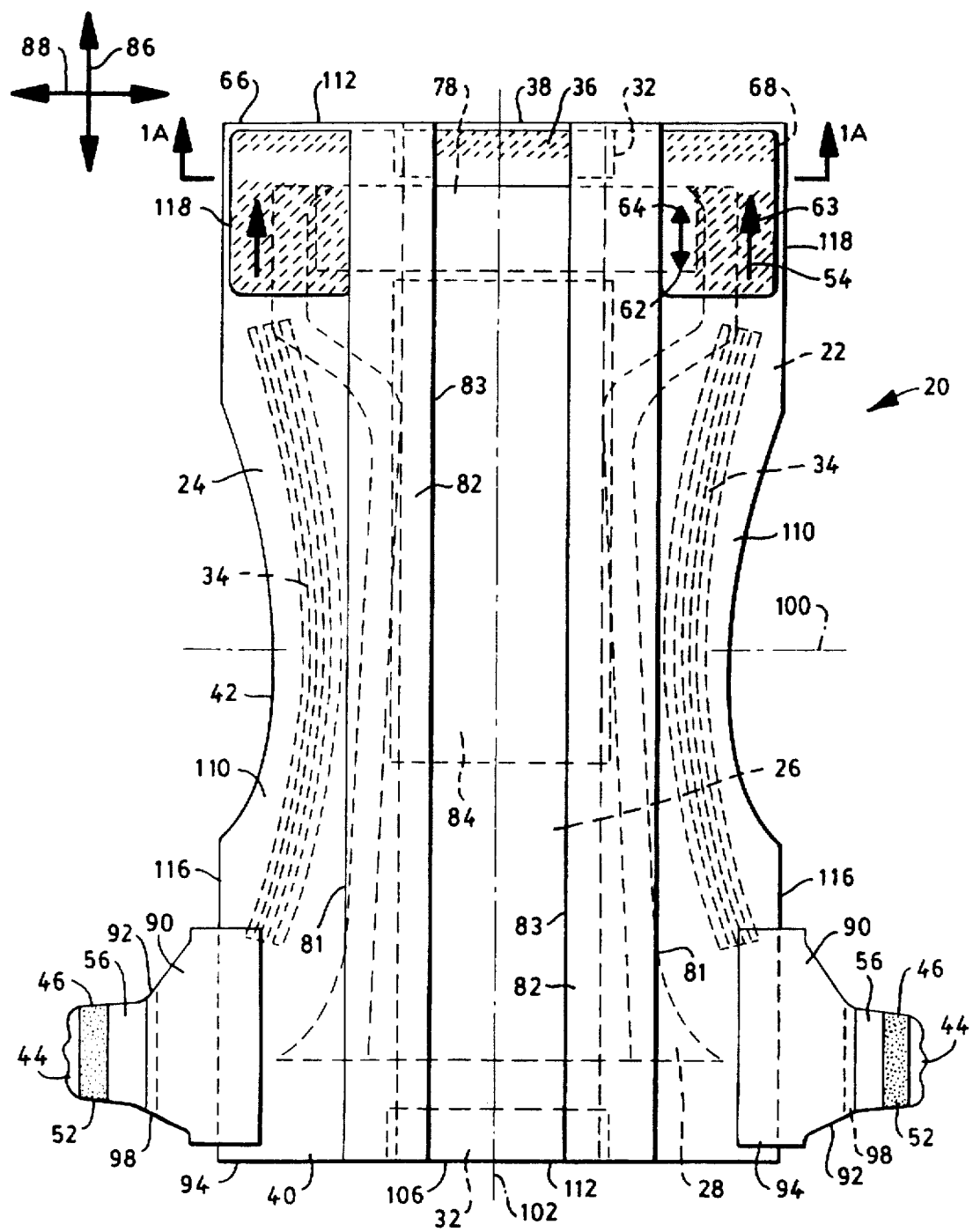
FIG. 1 representatively shows a top view of a diaper article which incorporates the fit panel of the invention.
Figure 1A:
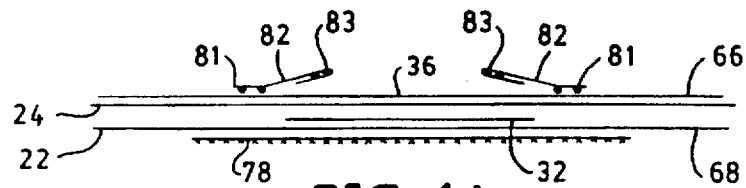
FIG. 1A representatively shows a schematic, lateral cross-sectional view of the article illustrated in FIG. 1.

With reference to FIGS. 1 and 1A, an article, such as the representatively shown disposable diaper 20, can include a first, front waistband section 38, a second, back waistband section 40, an intermediate section 42 interconnecting the front and back waistband sections, a longitudinal direction 86, a transverse cross-direction 88 and a laterally extending transverse line 100 which is longitudinally centered in the article 20. At least a first fit panel 36 is connected to an inside surface 66 of at least one of the waistband sections, and the fit panel has a direction-dependent coefficient of friction value along a non-isotropic, basis line 54 of the fit panel. A first coefficient of friction value is exhibited when sliding on the fit panel along the basis line in a first, inward basis direction generally toward the transverse lateral line and a different, second coefficient of friction value is exhibited when sliding on the fit panel along the basis line in a second, outward basis direction 64 which is opposite the first basis direction 62.

The distinctive fit panels incorporated into the various aspects of the invention can advantageously provide an effective positioning force which can tend to "walk" the waistband sections of the article in a direction which is relatively upward with respect to the wearer's body. In particular aspects, the direction-coefficient of friction value incorporated into the fit panels can cooperate with the movements of the wearer to generate an operative "walking" effect for repositioning the diaper. As a result, the article can provide improved fit with less sagging and with less gapping between the edges of the article and the wearer.

The article of the invention can be particularly configured to provide the absorbent disposable diaper 20. The diaper can, for example, include a backsheet layer 22, a liquid permeable topsheet layer 24 connected and integrated with the backsheet layer, and an absorbent structure, such as the absorbent body 26, which is sandwiched between the backsheet and topsheet layers.

In its various aspects, the present invention can advantageously reduce the sagging and drooping of the intermediate, crotch region of the garment, and can better maintain the desired fit around the wearer's waist region. When incorporated into an absorbent article, the invention can reduce undesired gapping and leakage.

With reference to FIGS. 1 and 1A, the invention provides an absorbent garment article, such as diaper 20, having a longitudinal, length-wise direction 86, and a lateral, crosswise direction 88. The front waistband section 38 has a laterally opposed, front pair of side edge regions 118, the rear waistband section 40 has a laterally opposed, rear pair of side edge regions, 116, and the intermediate section 42 interconnects the front and rear waistband section and provides a diaper crotch region. The article backsheet layer 22 has an appointed fastener landing zone 78 disposed on an outward surface of the backsheet layer. The liquid permeable topsheet layer 24 is superposed in facing relation with the backsheet layer 22, and the absorbent body 26 is operably connected and affixed between the backsheet layer 22 and topsheet layer 24.

FIG. 1 is a representative plan view of the representative disposable diaper 20 of the present invention in its flat-out, uncontracted state (i.e., with substantially all elastic induced gathering and contraction removed). Portions of the structure are partially cut away to more clearly show the interior construction of the diaper article, and the bodyside surface of the diaper which contacts the wearer is facing the viewer. The outer edges of the diaper define a periphery with longitudinally extending side edge margins 110 and laterally extending end edge margins 112. The side edges define leg openings for the diaper, and optionally, are curvilinear and contoured. The end edges are shown as straight, but optionally, may be curvilinear. The article has a first waistband section, such as rear waistband section 40, a second waistband section, such as front waistband section 38, and an intermediate section 42 which interconnects the first and second waistband sections.

The diaper 20 typically includes a porous, liquid permeable topsheet 24; a substantially liquid impermeable backsheet 22; an absorbent structure 26, positioned and connected between the topsheet and backsheet; a surge management portion 84; and elastomeric members, such as leg elastics 34 and waist elastics 32. The surge management portion is positioned in a liquid communication with a retention portion of the absorbent structure, and the topsheet 24, backsheet 22, absorbent structure 26, surge management portion 84 and elastic members 34 and 32 may be assembled together into a variety of well-known diaper configurations. The diaper can additionally include a system of containment flaps 82, and side panel members 90 which may be elasticized or otherwise elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 16, 1993 (attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995 (attorney docket No. 11,186); in U.S. patent application Ser. No. 286,086 of D. Fries, entitled A PROCESS FOR ASSEMBLING ELASTICIZED EAR PORTIONS and filed Aug. 3,1994 (attorney docket No. 11,169); and in U.S. patent application Ser. No. 08/415,383 of D. Fries, entitled AN ASSEMBLY PROCESS FOR A LAMINATED TAPE and filed Apr. 3, 1995 (attorney docket No. 11,950). The disclosures of the above-described documents are incorporated herein by reference in a manner that is consistent (not in conflict) herewith.

Diaper 20 generally defines the longitudinally extending length direction 86 and the laterally extending width direction 88, as representatively shown in FIG. 1. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 24 and backsheet 22 may be generally coextensive, and may have length and width dimensions which are generally larger than and extend beyond the corresponding dimensions of the absorbent structure 26 to provide for the corresponding side margins 110 and end margins 112. Topsheet 24 is associated with and superimposed on backsheet 22, thereby defining the periphery of the diaper 20. The waistband regions comprise those portions of the diaper, which when worn, wholly or partially cover or encircle the waist or mid-lower torso of the wearer. The intermediate, crotch region 42 lies between and interconnects the waistband regions 38 and 40, and comprises that portion of the diaper which, when warm, is positioned between the legs of the wearer and covers the lower torso of the wearer. Thus, the intermediate crotch region 42 is an area where repeated fluid surge typically occur in the diaper or other disposable absorbent article. Backsheet 22 can typically be located along an outer-side surface of the absorbent body 26 and may be composed of a liquid permeable material, but desirably comprises a material which is configured to be substantially impermeable to liquids.

For example, a typical backsheet can be manufactured from a thin plastic film, or other flexible, substantially liquid-impermeable material. As used in the present specification, the term "flexible" refers to materials which are compliant and which will readily conform to the general shape and contours of the wearer's body. Backsheet 22 prevents the exudates contained in absorbent body 26 from wetting articles, such as bedsheets and overgarments, which contact diaper 20. In particular embodiments of the invention, backsheet 22 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or nonwoven fibrous web layer which has been totally or partially constructed or treated to impart the desired levels of liquid impermeability to selected regions that are adjacent or proximate the absorbent body. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene blown film and a 0.7 ounce per square yard (23.8 gsm) polypropylene spunbond material (2 denier fibers). A material of this type forms the outercover of a HUGGIES® SUPREME diaper, which is commercially available from Kimberly-Clark Corporation. The backsheet 22 typically provides the outer cover of the article. Optionally, however, the article may include a separate outer cover component member which is additional to the backsheet.

Backsheet 22 may alternatively include a micro-porous, "breathable" material which permits gases, such as water vapor, to escape from absorbent body 26 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In the various configurations of the invention, where a component such as the backsheet 22 or the containment flaps 82 are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated 31 Dec. 1968.

The size of the backsheet 22 is typically determined by the size of absorbent body 26 and the particular diaper design selected. Backsheet 22, for example, may have a generally T-shape, a generally I-shape or a modified hourglass shape, and may extend beyond the terminal edges of absorbent body 26 by a selected distance, such as a distance within the range of about 1.3 centimeters to 2.5 centimeters (about 0.5 to 1.0 inch), to provide at least a portion of the side and end margins.

Topsheet 24 presents a body-facing surface which is compliant, soft-feeling, and non-irritating to the wearer's skin. Further, the topsheet 24 can be less hydrophilic than absorbent body 26, and is sufficiently porous to be liquid permeable, permitting liquid to readily penetrate through its thickness to reach the absorbent body. A suitable topsheet layer 24 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 24 is typically employed to help isolate the wearer's skin from liquids held in absorbent body 26.

Various woven and nonwoven fabrics can be used for topsheet 24. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 24 is a nonwoven, spunbond polypropylene fabric composed of about 2.8–3.2 denier fibers formed into a web having a basis weight of about 22 gsm and density of about 0.06 gm/cc. The fabric is surface treated with about 0.28% Triton X-102 surfactant. The surfactant can be applied by any conventional means, such as spraying, printing, brush coating or the like.

The topsheet 24 and backsheet 22 are connected or otherwise associated together in an operable manner. As used herein, the term "associated" encompasses configurations in which topsheet 24 is directly joined to backsheet 22 by affixing topsheet 24 directly to backsheet 22, and configurations wherein topsheet 24 is indirectly joined to backsheet 22 by affixing topsheet 24 to intermediate members which in turn are affixed to backsheet 22. Topsheet 24 and backsheet 22 can, for example, be affixed directly to each other in the diaper periphery by attachment means (not shown) such as adhesive bonds, sonic bonds, thermal bonds, pinning, stitching or any other attachment means known in the art, as well as combinations thereof. For example, a uniform continuous layer of adhesive, a patterned layer of adhesive, a sprayed pattern of adhesive or an array of separate lines, swirls or spots of construction adhesive may be used to affix topsheet 24 to backsheet 22. It should be readily appreciated that the above-described attachment means may also be employed to suitably interconnect, assemble and/or affix together the various other component parts of the articles which are described herein.

The absorbent body 26 provides an absorbent structure which can include a retention portion, such as the shown absorbent pad composed of selected hydrophilic fibers and high-absorbency particles, for holding and storing absorbed liquids and other waste materials. The absorbent body is positioned and sandwiched between topsheet 24 and backsheet 22 to form diaper 20. The absorbent body has a construction which is generally compressible, conformable, non-irritating to the wearer's skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of absorbent body 26. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent body structure 26 can comprise a matrix of hydrophilic fibers, such as a web of cellulosic fluff, mixed with particles of high-absorbency material. In particular arrangements, absorbent body 26 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in absorbent body 26 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 26. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and preferably is within the range of about 550–750 gsm to provide desired performance.

To improve the containment of the high-absorbency material, absorbent body structure 26 can include an overwrap, such as wrap sheet 28, which is placed immediately adjacent and around absorbent body 26 and may be bonded to the absorbent structure and to the various other components of the article. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 28, or at least the bodyside layer of the wrap sheet, may comprise a meltblown web composed of meltblown fibers, such as meltblown polypropylene fibers. Another example of absorbent wrap 28 may comprise a low porosity cellulosic web, such as a tissue composed of an approximately 50/50 blend of hardwood/softwood fibers.

The absorbent wrap 28 may comprise a multi-element wrapsheet which includes a separate bodyside wrap layer and a separate outerside wrap layer, each of which extends past all or some of the peripheral edges of absorbent body 26. Such a configuration of the wrap sheet can, for example, facilitate the formation of a substantially complete sealing and closure around the peripheral edges of absorbent body 26. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of absorbent wrap 28 can extend at least about ½ inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 28 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

Diaper 20 can also include a surge management layer 84 which helps to decelerate and diffuse surges of liquid that may be introduced into the absorbent body of the article. In the illustrated embodiment, for example, surge layer 84 can be located on an inwardly facing body side surface of topsheet layer 24. Alternatively, surge layer 84 may be located adjacent to an outer side surface of topsheet 24. Accordingly, the surge layer would then be interposed between topsheet 24 and absorbent body 26. Examples of suitable surge management layers 84 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4,1994 (attorney docket No. 11,256); and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 (attorney docket No. 11,387); the entire disclosures of which are hereby incorporated by reference in a manner that is consistent herewith.

The leg elastic members 34 are located in the lateral side margins 110 of diaper 20, and are arranged to draw and hold diaper 20 against the legs of the wearer. The elastic members are secured to diaper 20 in an elastically contractible condition so that in a normal under strain configuration, the elastic members effectively contract against diaper 20. The elastic members can be secured in an elastically contractible condition in at least two ways, for example, the elastic members may be stretched and secured while diaper 20 is in an uncontracted condition. Alternatively, diaper 20 may be contracted, for example, by pleating, and the elastic members secured and connected to diaper 20 while the elastic members are in their relaxed or unstretched condition. Still other mechanisms, such as heat-shrink elastic material, may be used to gather the garment.

In the embodiment illustrated in FIG. 1, leg elastic members 34 extend essentially along the complete length of the intermediate crotch region 42 of diaper 20. Alternatively, elastic members 34 may extend the entire length of diaper 20, or any other length suitable providing the arrangement of elastically contractible lines desired for the particular diaper design.

Elastic members 34 may have any of a multitude of configurations. For example, the width of the individual elastic members 34 may be varied from 0.25 millimeters (0.01 inch) to 25 millimeters (1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 20 with sprayed or swirled patterns of hotmelt adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of Lycra elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, diaper 20 can include a waist elastic 32 positioned in the longitudinal margins of either or both of front waistband 38 and rear waistband 40. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

Diaper 20 can also include a pair of elasticized containment flaps 82 which extend generally length-wise along the longitudinal direction 86 of the diaper. The containment flaps are typically positioned laterally inboard from leg elastics 34, and substantially symmetrically placed on each side of the lengthwise, longitudinal centerline of the diaper. In the illustrated arrangements, each containment flap 82 has a substantially fixed edge portion 81 and a substantially moveable edge portion 83, and is operably elasticized to help each containment flap to closely contact and conform to the contours of the wearer's body. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT (attorney docket No. 11,375), the disclosure of which is hereby incorporated by reference in a manner that is consistent herewith.

In optional, alternative configurations of the invention, diaper 20 may include elasticized waist flaps, such as those described in U.S. Pat. No. 4,753,646 issued Jun. 28, 1988, to K. Enloe, and in U.S. patent application Ser. No. 560,525 of D. Laux et al. entitled AN ABSORBENT ARTICLE WITH IMPROVED ELASTIC MARGINS AND CONTAINMENT SYSTEM and filed Dec. 18, 1995 (attorney docket No. 11091), the entire disclosures of which are hereby incorporated by reference in a manner that is consistent herewith. Similar to the construction of the containment flaps, the waist flaps may be composed of a wettable or non-wettable material, as desired. The waist flap material may be substantially liquid-impermeable, permeable to only gas, or permeable to both gas and liquid.

To provide a refastenable fastening system, diaper 20 can include an appointed landing zone 78 (e.g. FIG. 1A), which can provide an operable target area for receiving a releasable attachment of the fastener tabs 44 thereon. In particular embodiments of the invention, the landing zone patch can be positioned on the outward surface of backsheet layer 22 and is located on the front waistband portion 38 of the diaper. The fastening mechanism between the landing zone and the fastener tabs 44 may be adhesive, cohesive, mechanical or combinations thereof. A configuration which employs a releasable, interengaging mechanical fastening system can, for example, locate a first portion of the mechanical fastener on the landing zone 78 and a second, cooperating portion of the mechanical fastener on the fastener tab 44. For example, with a hook-and-loop fastener, the hook material 46 can be operably connected to the fastener tabs 44 and the loop material 80 can be operably connected to the landing zone 78. Alternatively, the loop material can be operably connected to the fastener tabs 44 and the hook material can be operably connected to the landing zone.

In the various embodiments of the invention, a tape fastener tab 44 can be located at either or both of lateral end regions 116 and 118 of either or both of the waistbands 38 and 40. The representatively shown embodiment, for example, has the fasteners tabs 44 located at the distal side edges of the rear waistband 40.

With reference to FIG. 1, for example, the article can include a system of side panel members 90. In particular arrangements, each side panel member 90 extends laterally from the opposed lateral ends of at least one waistband portion of backsheet 22, such as the representatively shown rear waistband portion 40, to provide terminal side sections of the article. In addition, each side panel can substantially span from a laterally extending, terminal waistband edge 106 to approximately the location of its associated and corresponding leg opening section of the diaper. Diaper 20, for example, has a laterally opposed pair of leg openings formed by appointed, medial sections of the shown pair of longitudinally extending, side edge regions 110 (FIG. 1). Each side panel can span a longitudinal distance of at least about 4 cm, optionally may span a longitudinal distance of at least about 5 cm, and alternatively may span a distance of at least about 6 cm to provide improved fit.

In the various configurations of the invention, the side panels may be integrally formed with a selected diaper component. For example, side panels 90 can be integrally formed from the layer of material which provides backsheet layer 22, or may be integrally formed from the material employed to provide topsheet 24. In alternative configurations, the side panels 90 may be provided by one or more separate members that are connected and assembled to the backsheet 22, to the topsheet 24, in between the backsheet and topsheet, and in various fixedly attached combinations of such assemblies.

In particular aspects of the invention, each of the side panels 90 may be formed from a separately provided piece of material which is then suitably assembled and attached to the selected front and/or rear waistband portion of the diaper article. In the illustrated embodiments of the invention, for example, each side panel 90 is attached to the rear waistband portion of backsheet 22 along a side panel attachment zone 94, and can be operably attached to either or both of the backsheet and topsheet components of the article. The shown configurations have the inboard, attachment zone region of each side panel overlapped and laminated with its corresponding, lateral end edge region of the waistband section of the article. The side panels extend laterally to form a pair of opposed waist-flap sections of the diaper, and are attached with suitable connecting means, such as adhesive bonding, thermal bonding, ultrasonic bonding, clips, staples, sewing or the like. Desirably, the side panels extend laterally beyond the terminal side edges of the backsheet layer and topsheet layer at the attached waistband section of the article.

The side panels 90 may be composed of a substantially non-elastomeric material, such as polymer films, woven fabrics, nonwoven fabrics or the like, as well as combinations thereof. In particular aspects of the invention, side panels 90 are composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 88. For example, suitable meltblown elastomeric fibrous webs for forming side panels 90 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the side panels 90 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

Where the side panels 90 are composed of a material which has been elasticized or otherwise constructed to be elastomerically stretchable, the elastomeric side panels can desirably provide an elongation at peak load of at least about 30 percent when subjected to a tensile force load of 0.33 pounds per lineal inch of the sample dimension that is measured perpendicular to the direction of the applied load (about 0.58 Newtons/cm). Alternatively, the elastomeric side panel material can provide an elongation of at least about 100%, and optionally can provide an elongation of at least about 300% to provide improved performance.

Each of the side panels 90 extends laterally from opposed lateral ends of at least one waistband section of the diaper 20. In the shown embodiment, each side panel extends laterally from opposed lateral ends of the rear waistband section of the backsheet 22. Each of the side panels includes a relatively outboard, terminal free end region 92 which has a longitudinally extending length dimension. Each side panel also has a laterally extending width dimension and a base region 94 which has a lapped, construction bond attachment to either or both of the topsheet and backsheet layers. The illustrated side panels have a tapered or otherwise contoured shape in which the base length of the base region 94 is smaller than the length of the relatively outboard free end region 92. Optionally, the length of the base region 94 may be larger than the length of the relatively outboard free end region 92. Alternatively, the side panels may have a substantially rectangular shape or a substantially trapezoidal shape.

A stress beam section 98 can be constructed on each of the side panels 90 along its outboard, free end region 92 to more evenly distribute tensile stresses across the side panel area. The stress beam section is configured with a relatively high stiffness value, and in desired configurations, the stress beam section extends along substantially the entire longitudinal length of the side panel outboard region 92. A fastening tab 44 can be connected to extend laterally from the stress beam section of each of the side panels 90 for securing the waistband sections of the article about a wearer during the use of the article.

In a particular aspect of the invention, each fastening tab 44 includes a carrier layer 56 which interconnects an inboard edge of the selected fastening component, such as the shown hook member 46, to the outboard edge region of its associated and corresponding side panel 90. The carrier layer has a laterally inboard, first side region and a laterally outboard, second side region. The first side region is laminated, or otherwise connected and affixed, to the side panel with an operable construction bond. The side panel material, the carrier layer material and the configuration of the construction bond are constructed and arranged to form the operative stress beam section 98. Optionally, an additional layer of reinforcement material may be included along the stress beam region to increase the stiffness of the beam and to further improve its ability to spread stresses along the longitudinal dimension of the side panel. The inboard region of the carrier layer 56 may have a longitudinal extent which is less than the longitudinal dimension 94 of the outboard, free edge portion 92 of the side panel 90. Alternatively, the carrier layer 56 can have a longitudinal extent which is substantially equal to (e.g. FIG. 1) or greater than the longitudinal dimension 94 of the outboard portion of the side panel.

The member of hook material 46 is laminated, or otherwise connected and affixed, to the outboard region of the carrier layer with an operable construction attachment. In particular, the shown hook member 46 is laminated to a inward, bodyside surface of the carrier layer with the hook elements extending generally inwardly of the article. With the illustrated arrangement, the outboard, laterally distal edge of the second carrier edge region is coterminous with the outboard, laterally distal edge of the hook member 46. Alternatively, the outboard, laterally distal edge of the second carrier edge region may be spaced laterally inboard from the terminal, laterally distal edge of the hook member 46. In either configuration, the laterally distal edge of the hook member 46 provides the laterally terminal edge of the article.

The longitudinally extending, relatively outboard edge of the side panel member 90 may be spaced from the longitudinally extending, relatively inboard edge of the selected fastening region by a carrier spacing distance. More particularly, the outboard edge of the side panel member 90 can also be spaced from the relatively inboard edge of the hook member 46 by the carrier spacing distance. The spacing distance optionally has a lateral extent which is equal to or greater than the lateral extent of the fastening region. In addition, the inwardly facing, bodyside surface of the carrier layer 56 is constructed to have a limited, mechanical interengageability with the hook elements 52. As a result, the fastener tab 44 can be folded along a longitudinally extending fold line to selectively locate and configure the fastening region in a storage position with the hook elements placed and held against the bodyside surface of the carrier layer 56.

The level of engagement between the hook material and the carrier layer need only be enough to maintain the storage position. For example, the engagement may provide a single-peak, peel force value within the range of about 1–50 grams of force. Larger levels of peel force may be provided, but such levels can make it more cumbersome to separate and move the hook material away from its storage position into its ordinary, primary fastening position. Where the bodyside surface of the carrier layer is already an exposed woven or nonwoven fabric, the desired engagement can be provided by the ordinary interaction between the fabric matrix and the hook elements. Where the bodyside surface of the carrier layer is not an exposed fabric, the desired engagement can be provided by attaching an operable component of a fabric or other mesh-like material onto the bodyside surface.

In particular configurations of the invention, the material of carrier layer 56 can be composed of a substantially non-elastomeric material, such as polymer films, woven fabrics, nonwoven fabrics or the like, as well as combinations thereof. Alternatively, the carrier web material may be composed of a substantially elastomeric material, such as a stretch-bonded-laminate (SBL) material, a neck-bonded-laminate (NBL) material, an elastomeric film, an elastomeric foam material, or the like, as well as combinations thereof. The elastomeric material is elastomerically stretchable at least along the lateral direction 88. In the shown arrangement, for example, the carrier web material is composed of a spunbond-meltblown-spunbond (SMS) fabric having a core of meltblown fibers sandwiched between two facing layers of spunbond fibers to provide a total composite basis weight within the range of about 50–67 g/m² (about 1.5–2 oz/yd²). As another example, the carrier web material may be entirely composed of a nonwoven spunbond fabric having a basis weight within the range of about 50–67 g/m² (about 1.5–2 oz/yd²).

The mechanical fasteners cooperatively employed with the various configurations of the invention can be provided by mechanical-type fasteners such as hooks, buckles, snaps, buttons and the like, which include cooperating and complementary, mechanically interlocking components. In particular aspects of the invention, the fastening means can be provided by a hook-and-loop fastener system, a mushroom-and-loop fastener system, or the like (collectively referred to as hook-and-loop fasteners). Such fastening systems generally comprise a "hook" or hook-like, male component, and a cooperating "loop" or loop-like, female component which engages and releasably interconnects with the hook component. Desirably, the interconnection is selectively releasable. Conventional systems are, for example, available under the VELCRO trademark.

Examples of suitable hook-and-loop fastening systems are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al.; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer 56 are described in U.S. patent application Ser. No. 08/603,477 of A. Long et al., entitled MECHANICAL FASTENING SYSTEM WITH GRIP TAB and filed Mar. 6, 1996 (attorney docket No. 12,563), the entire disclosure of which is hereby incorporated by reference in a manner which is consistent herewith.

In a typical configuration of a hook-and-loop fastening system, the hook material member 46 is operably connected to the fastening tab 44, and the loop material 80 is employed to construct at least one cooperating landing zone 78. The landing zone, for example, can be suitably positioned on the exposed, outward-side surface of the backsheet 22. As previously mentioned, an alternative configuration of the hook-and-loop fastening system may have the loop material secured to the fastener tab 44 and may have the hook material employed to form the landing zone 78.

In particular aspects of the invention, the hook material member 46 can be of the type referred to as micro-hook material. A suitable micro-hook material is distributed under the designation CS200 and is available from 3M Company, a business having offices in St. Paul, Minn. The micro-hook material can have hooks in the shape of mushroom "caps", and can be configured with a hook density of about 1600 hooks per square inch; a hook height which is within the range of about 0.033–0.097 cm (about 0.013 to 0.038 inch); and a cap width which is within the range of about 0.025–0.033 cm (about 0.01 to 0.013 inch). The hooks are attached to a base film substrate having a thickness of about 0.0076–0.01 cm (about 0.003–0.004 inch) and a Gurley stiffness of about 15 mgf.

Another suitable micro-hook material is distributed under the designation VELCRO CFM-29 1058, and is available from VELCRO U.S.A., Inc., a business having offices in Manchester, N.H. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch) and the member of hook material has a Gurley stiffness of about 12 mgf.

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. This instrument allows the testing of a wide variety of materials through the use of various lengths and widths in combination with the use of a 5, 25, 50, or 200 gram weight placed in one of three positions on the pointer of the apparatus. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness. The standard size sample has a width of 1" and a nominal length of 3" (actual length of 3.5"). The actual length of the sample is the nominal length, plus an additional 0.25" of length for holding in the clamp and another 0.25" of length for overlapping the vane. Tables of factors for taking scale readings generated with non-standard sized test samples and converting the readings to the stiffness of the standard size sample are given in the Instruction Manual for the Gurley Stiffness Tester provided by Teledyne Gurley. Accordingly, other designated dimensions for the test sample may also be conveniently employed, so long as the appropriate conversion factor is employed to determine the appropriate value which corresponds to the standard size sample.

In the various configurations of the invention, the loop material can be provided by a nonwoven, woven or knit fabric. For example, a suitable loop material fabric can be composed of a 2 bar, warp knit fabric of the type available from Guilford Mills, Inc., Greensborough, N.C. under the trade designation #34285, as well other of knit fabrics. Suitable loop materials are also available from the 3M Company, which has distributed a nylon woven loop under their SCOTCHMATE brand. The 3M Company has also distributed a linerless loop web with adhesive on the backside of the web, and 3M knitted loop tape.

In particular aspects of the invention, the loop material need not be limited to a discrete landing zone patch. Instead the loop material can, for example, be provided by a substantially continuous, outer fibrous layer which is integrated to extend over substantially the total exposed surface area of a cloth-like outer cover employed with the diaper 20. The resultant, cloth-like backsheet 22 can thereby provide the loop material for an operative "fasten anywhere" mechanical fastening system.

The fastening elements in the various constructions of the invention may be operably attached to its base layer by employing any one or more of the attachment mechanisms employed to construct and hold together the various other components of the article of the invention. Desirably, the fastening elements in the various fastening regions, may be integrally formed, such as by molding, co-extrusion or the like, along with the associated base layer. The base layer and the mechanical fastening elements can be formed from substantially the same polymer material, and there need not be a discrete step of attaching the fastening elements to an initially separate hook base layer. In the representatively shown configurations of the primary fastening region, for example, the illustrated hook elements 52 are integrally formed simultaneously with the hook base layer by coextruding the base layer and hook elements from substantially the same polymer material.

It should be readily appreciated that the strength of the attachment or other interconnection between the base layer and the attached fastening component should be greater than the peak force required to remove the fastener tab 44 from its releasable securement to the appointed landing zone of the article.

At least a first fit panel 36 connects to an inside surface 66 of at least one of the waistband sections. For example, the inside fit panel 36 may be located at and attached to the inside surface of the front waistband section 38 (e.g. FIG. 1), or the rear waistband section 40 (e.g. FIG. 2). Optionally, a first inside fit panel section can overlie and be attached to an inside surface of the front waistband section 38, and another, second inside fit panel section can be similarly attached to the inside surface of the rear waistband section 40 (e.g. FIG. 4).

The fit panel 36 has an anisotropic, direction-dependent coefficient of friction value along the basis line 54 of the fit panel. The basis line of the fit panel material is the line along which the panel material exhibits its relatively highest coefficient of friction value.

When sliding on the fit panel 36 along the basis line 54 in a first, relatively inward basis direction 62 which is directed generally toward the laterally extending, longitudinally-centered laterally extending line 100, the fit panel exhibits a first coefficient of friction value. When sliding on the fit panel 36 along the basis line 54 in a second outward basis direction 64 which is directed substantially opposite to the first basis direction 62, the fit panel exhibits a different, second coefficient of friction value. The coefficient of friction values are relative values determined from measurements of particular dynamic or kinetic coefficients of friction, and the values may be referred to as relative coefficients of friction. For the purposes of the present description, such coefficient of friction values can be determined by employing the Friction Testing procedure set forth in detail herein. With respect to the first and second basis directions, the maximal basis direction 63 is the direction of sliding along which the sliding object is resisted with the largest coefficient of friction provided by the fit panel material. Where a material has a "grain", such sliding movement may be referred to as moving "against the grain". In the various illustrations of the invention, the maximal basis direction is representatively indicated by the bold, single arrow directed along its associated basis line 54.

In desired arrangements of the invention, the first coefficient of friction value can be less than the second coefficient of friction value. Alternatively, the first coefficient of friction value can be greater than the second coefficient of friction value to provide particular performance advantages.

In particular aspects of the invention, the greater one of the first and second coefficient of friction values (the greater coefficient of friction value) can be not less than about 1.0. Alternatively, the greater coefficient of friction value can be not less than about 1.3, and optionally can be not less than about 1.4. In other aspects, the greater coefficient of friction value can be not more than about 2.4. Alternatively, the greater coefficient of friction value can be not more than about 2.1, and optionally can be not more than about 2.0 to provide desired performance advantages.

In still other aspects of the invention, the lesser one of the first and second coefficient of friction values (the lesser coefficient of friction value) can be not less than about 0.6. Alternatively, the greater coefficient of friction value can be not less than about 0.7, and optionally can be not less than about 0.8. In further aspects, the greater coefficient of friction value can be not more than about 1.9. Alternatively, the lesser coefficient of friction value can be not more than about 1.7, and optionally can be not more than about 1.5 to provide advantageous performance.

In yet other aspects of the invention, a ratio of the greater coefficient of friction value to the lesser coefficient of friction value (the greater-to-lesser coefficient of friction ratio) can be not less than about 1.15:1. Alternatively, the ratio of the greater coefficient of friction value to the lesser coefficient value can be not less than about 1.17:1, and optionally can be not less than about 1.19:1. In additional aspects, a ratio of the greater coefficient of friction value to the lesser coefficient of friction value can be not more than about 3.00:1. Alternatively, the ratio of the greater coefficient of friction value to the lesser coefficient value can be not more than about 2.80:1, and optionally can be not more than about 2.60:1 to provide improved performance.

To further assist in providing desired fit, the various configurations of the invention can have a structure wherein the arithmetic difference between the first and second coefficient of friction values (the lesser of the first and second coefficient of friction values subtracted from the greater of the values) can be not less than about 0.15. Alternatively, the arithmetic difference between the first and second coefficients of friction can be not less than about 0.2, and optionally can be not less than about 0.24.

In additional aspects, the various configurations of the invention can have a structure wherein the arithmetic difference between the first and second coefficient of friction values (the lesser of the first and second coefficient of friction values subtracted from the greater of the values) can be not more than about 1.5. Alternatively, the arithmetic difference between the first and second coefficients of friction can be not more than about 1.35, and optionally can be not more than about 1.15 to provide desired improvements in performance.

With the various aspects of the invention, the material of the fit panel 36 does not engage the wearer's skin or any supplemental fit panel 70 with an attachment which requires more than an insubstantial peeling force for removal or disengagement. In particular, the fit panel material provides substantially no adhesive or cohesive, peel force bonding to the skin or to another contacting layer.

The direction-dependent coefficient of friction value of various fit panels 36 and 70 can be provided by a woven or nonwoven fabric having a directional grain aligned substantially along the basis line 54. As representatively shown in FIG. 9, for example, an individual fit panel can include a fabric having a majority of its fibers configured with a directed orientation which is aligned substantially along the fabric grain. In addition, the individual fibers can have a fixed end and an opposed moveable loose end. A majority of the fiber are arranged non-perpendicular to the horizontal base plane of the fabric, and the fibers can be curled, bent, slanted or otherwise preferentially directed to point the loose ends of those fibers along an inclination line which has a horizontal directional component substantially along the basis line 54. As a result, when sliding along the basis line in a first direction, the fabric exhibits a first coefficient of friction value. When sliding along the fabric basis line in a direction opposite to the first direction, the fabric exhibits a second coefficient of friction value which differs from the first coefficient of friction value by a selected amount.

The fit panels incorporated with the various aspects and configurations of the present invention can comprise a nonwoven fabric. Examples of such nonwoven fabrics can include flocked, nonwoven fabrics treated or otherwise processed to orient the surface fibers in arrangements which are non-perpendicular to the general plane of the fabric, and are biased to point substantially along a same, common direction.

Alternatively, the various fit panels incorporated with the various aspects and configurations of the present invention can comprise a woven fabric. Examples of suitable woven fabrics can include velvet fabrics, pleated fabrics and the like, as well as combinations thereof.

Optionally, the various fit panels incorporated into the present invention can comprise a nonfabric, such as a modified film. Examples of such nonfabric materials can include punctured films, films with molded projecting elements, films with embossments or molded recesses, and the like, as well as combinations thereof. The modifications are appropriately configured to impart a non-isotropic coefficient of friction when sliding along the surface of the modified film. For example, the fit panel may comprise a film material having a substrate with projecting elements which extend away from a surface of the substrate. The film material, and particularly the projecting elements, can thereby provide for a directional grain which is aligned substantially along the basis line of the material. A suitable modified film may be a molded polymer layer, such as a Microhook XMH-4130/CS-200 material available from 3M Corporation, a business having offices in St. Paul, Minn. The microhook material has a base layer with extending projections which are consistently oriented and preferentially biased along a substantially common direction.

In the various configurations of the invention, each fit panel extends a selected distance inwardly from the terminal side and end edges of the article, and extends over a selected panel area. Desirably, each fit panel has an operative area which is not less than about 1 $cm^2$. Alternatively, the fit panel area is not less than about 3 $cm^2$, and optionally is not less than about 5 $cm^2$. In other aspects, the fit panel area is not more than about 500 $cm^2$. Alternatively, the fit panel area is not more than about 350 $cm^2$, and optionally is not more than about 200 $cm^2$.

With reference to FIGS. 1 and 1A, the inside fit panel 36 can be laminated to a bodyside surface of the topsheet layer 24, and the containment flaps 82 can be arranged to overlie a bodyside surface of the topsheet layer. Alternatively, the inside fit panel 36 can be laminated to a bodyside surface of the topsheet layer 24, and can be arranged to overlie a bodyside surface of the containment flaps 82 (e.g. FIG. 7). As a result, a major portion of the inside fit panel 36 is arranged to contact the skin of the wearer. As representatively shown, the fit panel 36 can have a generally U-shape. The U-shape can be angular in configuration, as illustrated, or may be curvilinear. The base of the U-shape extends laterally along the longitudinally terminal edge region of the article. The extending arms of the U-shape extend longitudinally along the laterally terminal side edges of the article, with one extending arm positioned at each lateral side edge of the article. In addition, the relatively inboard edges of the extending arm sections of the U-shape can at least partially overlap their corresponding containment flaps 82 in a manner which does not interfere with the mobility of the inboard moveable edges 83 of the containment flaps.

The basis line 54 of the fit panel 36 extends along the longitudinal direction 86. In the representatively shown configuration, the coefficient of friction value exhibited when sliding on the fit panel along the relatively inward basis direction is less than the coefficient of friction value exhibited when sliding along the opposite, outward basis direction. Accordingly, the maximal basis direction 63 is along the relatively outward direction of the basis line 54.

The relatively larger coefficient of friction value is at least about 1.0. Alternatively, the relatively greater coefficient of friction value can be at least about 1.3, and optionally can be at least about 1.6.

The relatively smaller coefficient of friction value is desirably not more than about 2.0. Alternatively, the relatively smaller coefficient of friction value can be not more than about 1.7, and optionally can be not more than about 1.4.

Figure 2:
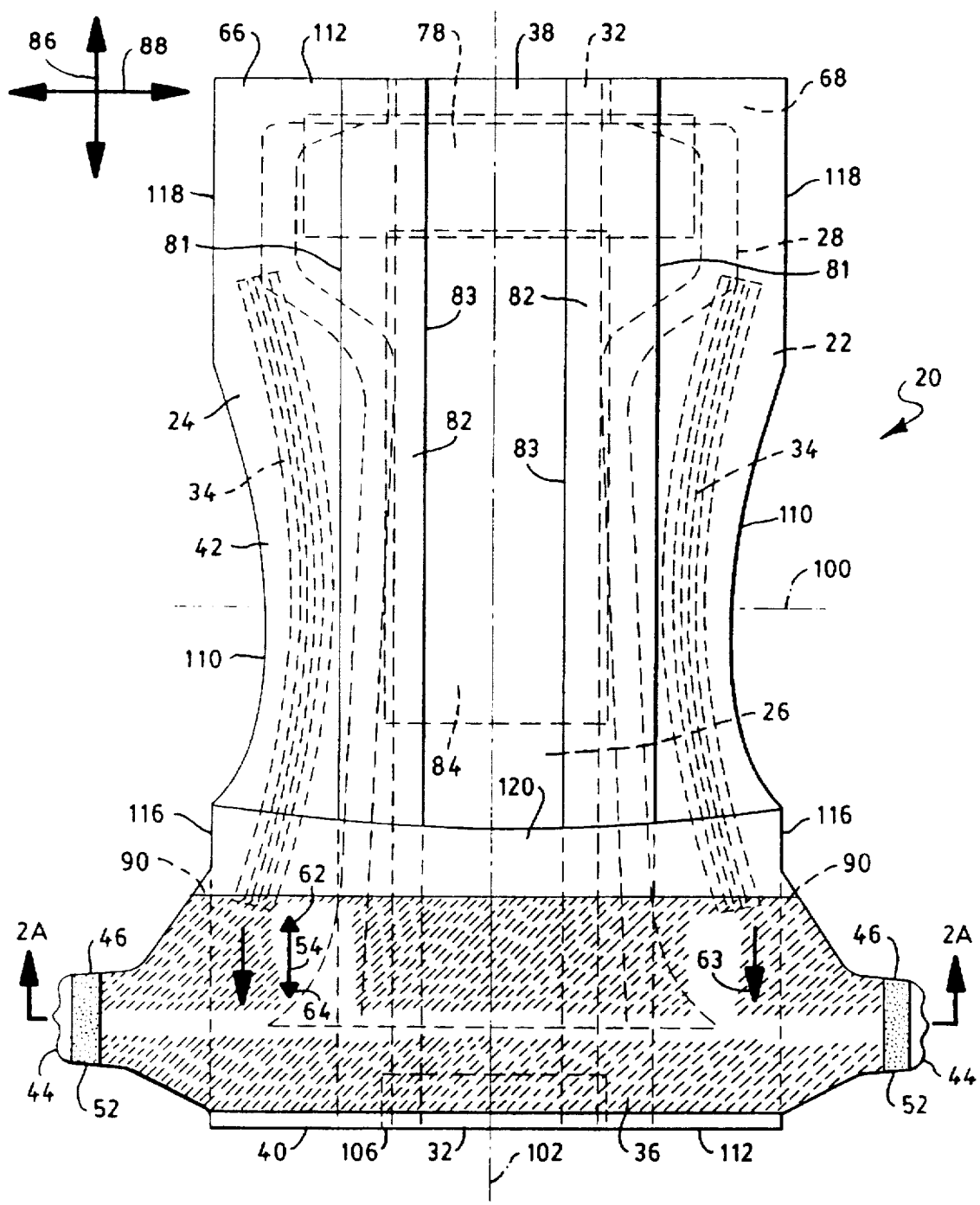
FIG. 2 representatively shows a top view of an article which incorporates an aspect of the invention having the fit panel positioned on a facing surface of a waist flap member.
Figure 2A:
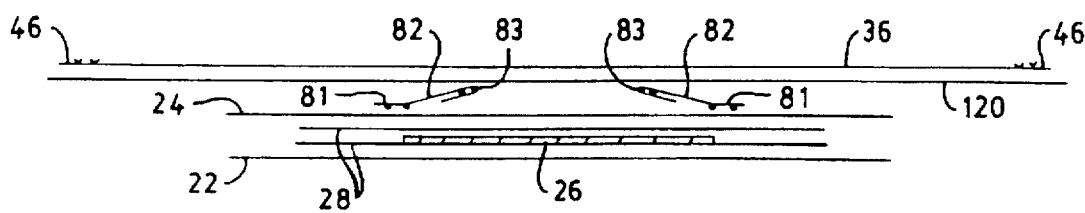
FIG. 2A representatively shows a schematic, lateral cross-sectional view of the article illustrated in FIG. 2.

With reference to FIGS. 2 and 2A, the article can include a waist flap member 120 arranged to overlie the bodyside surface of the topsheet layer 24 along at least one selected waistband section of the article, such as the illustrated rear waistband section 40. Optionally, a waist flap member 120 can be similarly located at either or both of the waistband sections 38 and 40. In desired arrangements, the waist flap member 120 is constructed to be elastomerically contractible and extendible at least along the cross-direction 88. In the illustrated arrangement, the inside fit panel 36 is a separately provided component which is suitably laminated and attached to the bodyside surface of the waist flap member 120. Alternatively, the inside fit panel may be a component which is integrally formed with the material of the waist flap member. The fit panel portion extends selected distances inwardly from the terminal side and end edges of the article, and extends over a selected panel area.

The representatively shown configuration of the inside fit panel 36 includes a basis line 54 aligned substantially along the longitudinal direction 86. The coefficient of friction value exhibited when sliding along the outward basis direction is desirably greater than the coefficient of friction value exhibited when sliding along the inward basis direction, although the inverse configuration may optionally be employed. In the shown configuration, the maximal basis direction 63 is along the relatively outward direction of the basis line 54.

In another aspect, the fit panel 36 can further include an elasticizing mechanism for providing an elastomeric stretchability to the fit panel at least along the cross-dimension 88 of the article. The elasticizing mechanism can be provided by one or more elastomeric members which are affixed to the fit panel 36 in an elastically contractible condition, in a manner similar to that employed to attach the leg elastics 34 and waist elastics 32 in their elastically contractible condition. Alternatively, the elasticizing mechanism can be provided by constructing the fit panel from an elastomeric material.

Figure 3:
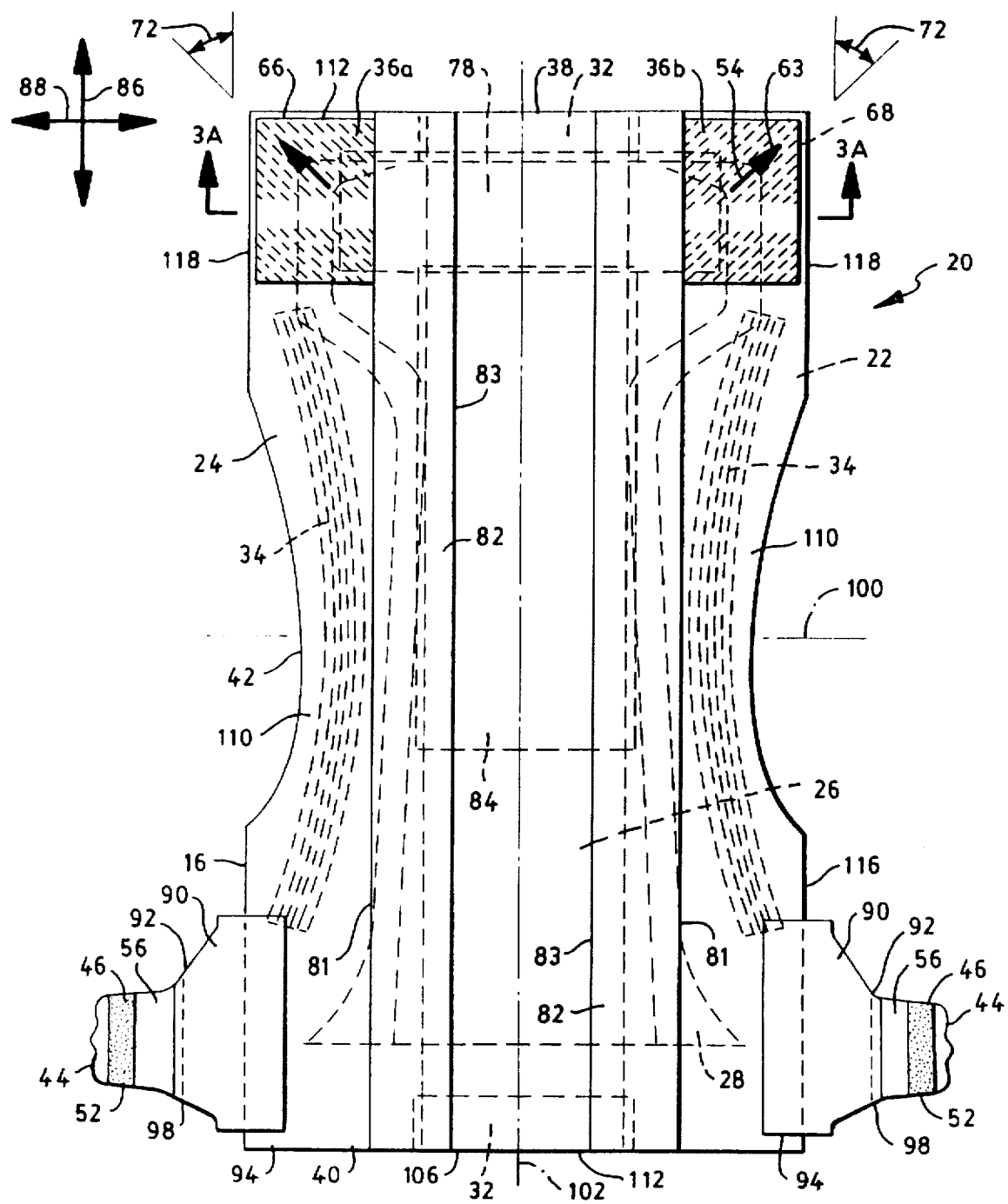
FIG. 3 representatively shows a top view of an article of the invention which incorporates a plurality of fit panel portions.
Figure 3A:
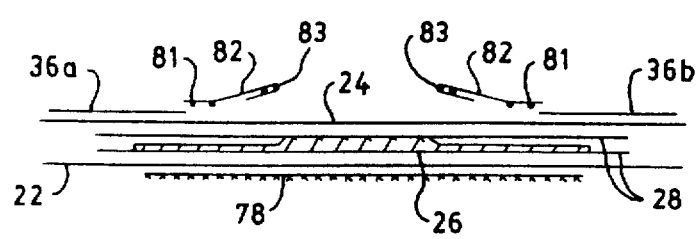
FIG. 3A representatively shows a schematic, lateral cross-sectional view of the article illustrated in FIG. 3.

With reference to FIGS. 3 and 3A, the internal fit panel 36 can be divided into a selected plurality of discrete, separately configured, inside fit sections. In the shown configuration, for example, a pair of spaced-apart, inside fit panel sections 36a and 36b are located adjacent to the two laterally opposed ends of the front waistband section 38 of the article. The fit panel sections can be suitably laminated and attached to the bodyside surface of the topsheet layer 24, and can also positioned to overlie a bodyside surface of the containment flaps 82. The illustrated fit panel portions are generally rectangular shaped, but may alternatively be configured with other rectilinear or curvilinear shapes, as desired. In a particular aspect of the illustrated arrangement, the laterally inboard edge of each fit panel section does not extend past the laterally inboard edge 83 of its associated containment flap 82.

The illustrated arrangement representatively shows a particular aspect of the invention wherein the basis line 54 of each fit panel section is slanted at a selected angle 72 relative to the longitudinal direction 86. As representatively shown, the slant angle 72 is the acute angle formed between the basis line 54 and the longitudinal direction 86 of the article. Desirably, the slant angle 72 is not less than about 5°. Alternatively, the slant angle can be not less than about 15°, and optionally can be not less than about 25°. In other aspects the slant angle 72 can be not more than about 85°. Alternatively, the slant angle can be not more than about 65°, and optionally can be not more than about 50°. In the shown configuration, the slant angle 72 is about 45 degrees. Accordingly, the basis line 54 of each fit panel portion 36a and 36b can diverge away from the longitudinally extending centerline 102 of the article, as determined when moving along the basis line toward the terminal, peripheral edges of the article. The shown arrangement has the maximal direction 63 extending along the generally outward direction of the basis line 54 toward the terminal boundary edges of the article.

Figure 4:
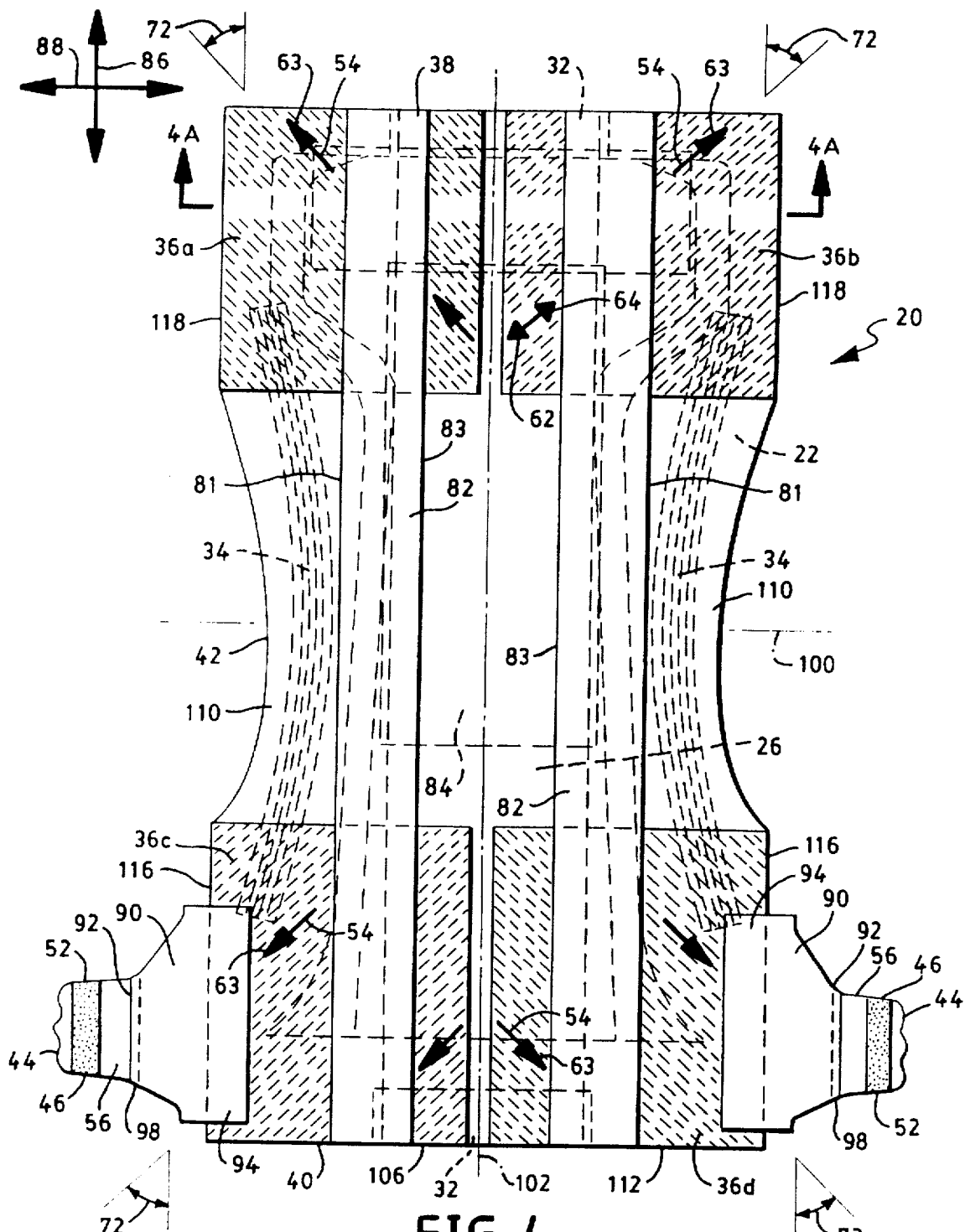
FIG. 4 representatively shows a top view of an article which incorporates an aspect of the invention having a plurality of fit panel sections placed on a facing surface of a topsheet layer.
Figure 4A:
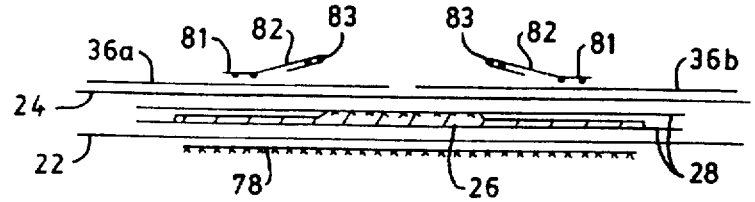
FIG. 4A representatively shows a schematic, lateral cross-sectional view of the article illustrated in FIG. 4.

With reference to FIGS. 4 and 4A, the inside fit panel 36 can include a plurality of fit panel portions, such as the illustrated four fit panel portions 36a, 36b, 36c, and 36d. The illustrated aspect of the invention has the fit panel portions operably laminated and affixed to the bodyside surface of the topsheet layer 24, and positioned adjacent to the side edge regions 116 and 118 of the rear waistband section 40 and front waistband section 38, respectively. Each of the fit panel portions extends selected distances inwardly from the terminal side and end edges of the article, and extends over a selected sectional area. In addition, the illustrated arrangement has the containment flaps 82 positioned to overlie onto a bodyside surface of each of the individual fit panel portions 36a, 36b, 36c, and 36d.

Desirably, each fit panel portion can have a sectional area of not less than about 15 $cm^2$. Alternatively, the sectional area of each fit panel portion can be not less than about 20 $cm^2$, and optionally can be not less than about 30 $cm^2$. In other aspects, each fit panel portion can have a sectional area of not more than about 300 $cm^2$. Alternatively, the sectional area of each fit panel portion can be not more than about 200 $cm^2$, and optionally can be not more than about 150 $cm^2$ to provide improved performance.

Each of the fit panel portions 36a, 36b, 36c and 36d can be individually and discretely configured. In the representatively shown arrangement, for example, each fit panel portion may also be discontinuous and spatially separated from the other fit panel portions. As a result, each fit panel portion can individually arranged to have its individual basis line positioned at a desired inboard or outboard slant angle, such as the shown slant angles 72, as measured relative to the longitudinal direction 86 of the article. As previously mentioned, the slant angle 72 is the acute angle formed between the individual basis line 54 and the longitudinal direction 86 of the article. The representatively shown arrangement has the maximal direction 63 extending along the generally outward direction of the basis line 54, toward the terminal boundary edges of the article.

In the illustrated arrangement, each of the fit panel portions 36a, 36b, 36c and 36d is a separately provided and separately configured element. Optional configurations of the invention can include one or more fit panel portions which are integrally formed with the material of another diaper component, such as the shown topsheet layer 24.

Figure 5:
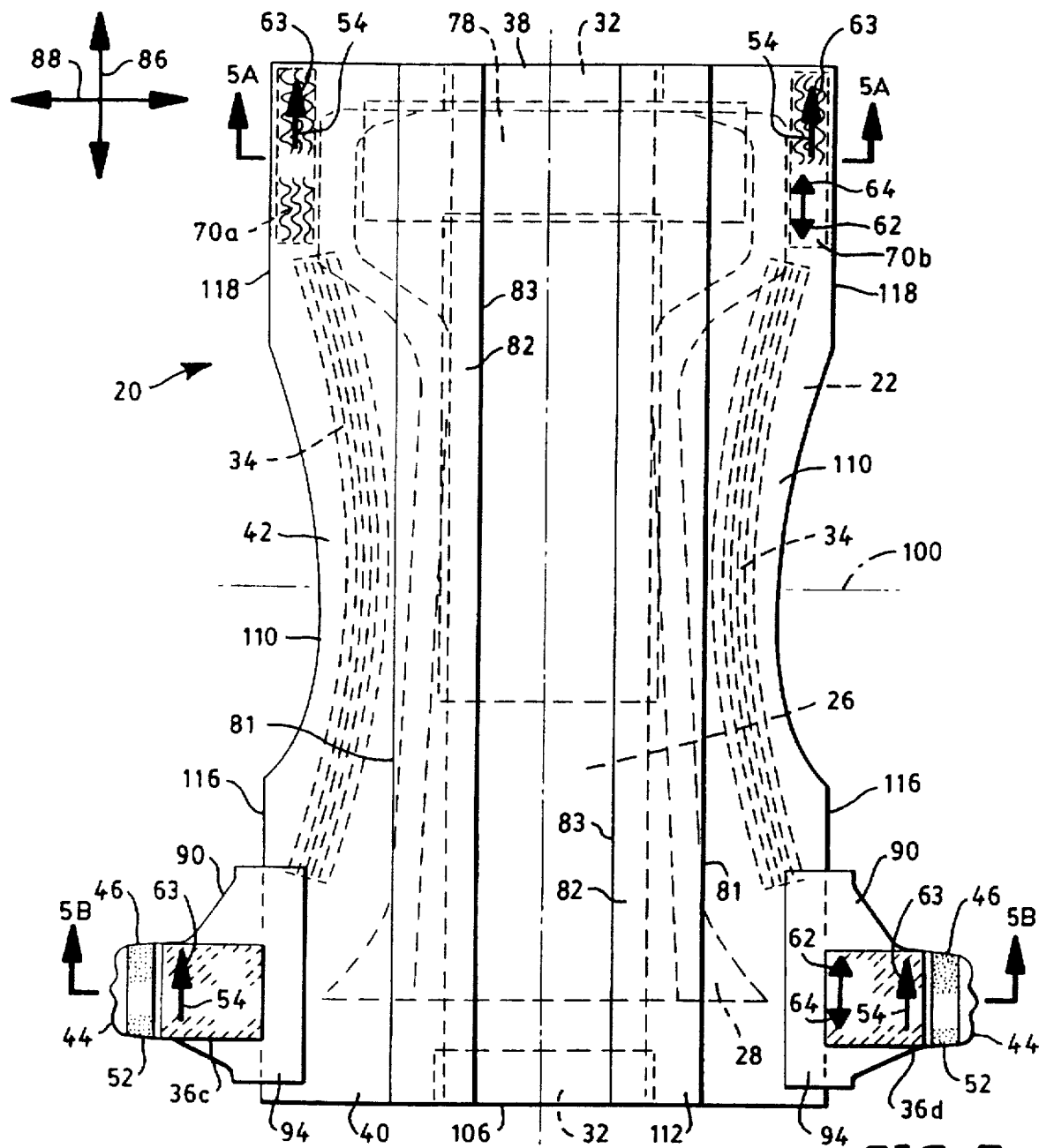
FIG. 5 representatively shows a top view of an article which incorporates an aspect of the invention having at least one supplemental fit panel.
Figure 5A:
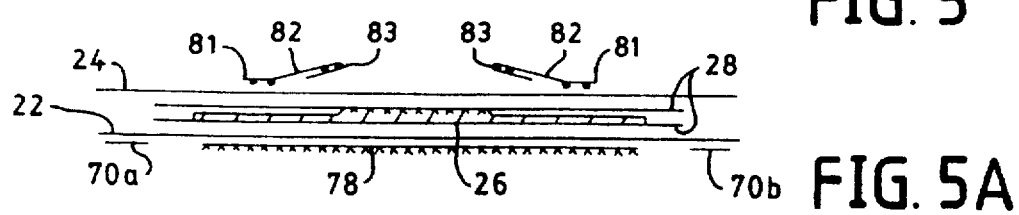
FIG. 5A representatively shows a schematic, lateral cross-sectional view along line 5A—5A of the article illustrated in FIG. 5.
Figure 5B:
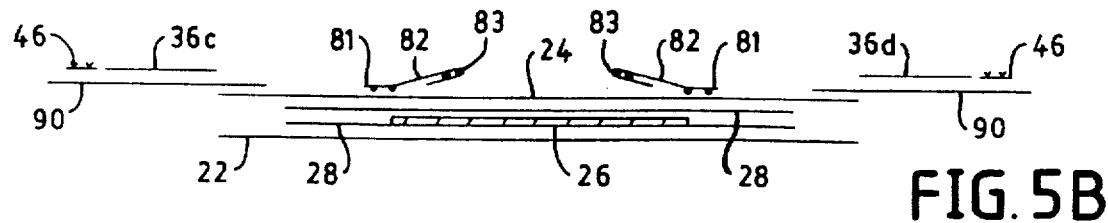
FIG. 5B representatively shows a schematic, lateral cross-sectional view along line 5B—5B of the article illustrated in FIG. 5.

With reference to FIGS. 5, 5A and 5B, the diaper article 20 can include at least one supplemental fit panel 70 connected to provide a substantially outermost surface of the article. As representatively shown, each of a pair of supplemental fit panel portions 70a and 70b can be connected adjacent to and along the front waistband, side edge regions 118. The illustrated supplemental fit panel portions are generally rectangular shaped, but may alternatively be configured with other rectilinear or curvilinear shapes, as desired. In addition, each of the supplemental fit panel portions may be substantially laterally aligned with the appointed fastening landing zone 78, as representatively shown.

Each of the supplemental fit panel portions 70a and 70b has a direction-dependent coefficient of friction value along its basis line 54, wherein the coefficient of friction value when sliding along a relatively inward first basis direction 62 is different than the coefficient of friction value exhibited when sliding along the relatively outward basis direction 64. In the illustrated configuration, for example, the coefficient of friction value exhibited when sliding in the relatively outward basis direction is greater than the coefficient of friction value exhibited when sliding along the supplemental fit panel portion along the relatively inward basis direction. Accordingly, the maximal direction 63 is along the relatively outward direction of the basis line 54. In addition, the example of the shown configuration has the basis line of the supplemental fit panel portions aligned substantially along the longitudinal direction 86. Optionally, the basis line of each supplemental fit panel portion may have a selected slant angle which is similar to the slant angle 72 described elsewhere in the present specification (e.g. FIG. 4).

As representatively shown, the article can include a selected plurality of inside fit panel portions, such as the illustrated fit panel portions 36c and 36d, which are overlaid and attached to the bodyside surface of the article, and are positioned substantially adjacent to the rear waistband side edge regions 116. In the shown configuration, each of the inside fit panel portions is laminated and bonded to provide a substantially innermost, bodyside surface of an associated side panel member 90. Desirably, each inside fit panel portion is substantially laterally aligned with the fastening region of its corresponding, adjacent fastener tab 44.

Each fit panel portion 36c and 36d can have a direction-dependent coefficient of friction value along its basis line 54. The shown configuration, for example, can have the basis line of each inside fit panel portion aligned substantially parallel with the longitudinal direction 86. In addition, the inside fit panel portion can exhibit a coefficient of friction value along an inward basis direction 62 which is different than the coefficient of friction value when exhibited along the opposite outward basis direction 64. In particular aspects, the coefficient of friction value exhibited when sliding along each fit panel portion along the first basis direction is greater than the coefficient of friction value exhibited when sliding in the outward basis direction.

Accordingly, the maximal basis direction 63 is along the relatively inward direction of the basis line 54.

In alternative configurations, the basis line of the inside fit panel portions can be arranged with a selected slant angle 72 relative to the longitudinal direction 86 of the article. Desirably, the slant angle 72 is selected to position the basis lines of the inside fit panel portions 36c and 36d at a slant angle 72 which is substantially equal to the slant angle 74 of the basis line of its longitudinally opposite, outside supplemental fit panel portion 70a and 70b, respectively.

When the fastener tabs 44 are fastened to the landing zone 78 to secure the front and rear waistband sections about a wearer, each of the inside fit panel portions 36c and 36d is arranged and configured to operatively contact and engage with its corresponding, longitudinally opposite supplemental fit panel portions 70a and 70b, respectively. When cooperatively engaged, the two associated and contacting fit panel portions (e.g. 70a and 36c) can have their respective basis lines substantially aligned with each other, with the maximal basis direction of one associated fit panel oriented approximately 180° from the maximal basis direction of the other associated fit panel. Thusly engaged, the ratio of the greater coefficient of friction value to the lesser coefficient of friction value, as determined with respect to a sliding of one fit panel portion over the other fit panel portion, can be greater than that measured when separately testing each of the engaged fit panel portions with respect to the substrates employed in the Friction Testing Procedure. The cooperatively engaged fit panel portions can be drawn across each other to determine a direction of greater coefficient of friction value and a direction of lesser coefficient of friction value. In this arrangement, the ratio of the greater coefficient of friction value to the lesser coefficient of friction value (the greater-to-lesser coefficient of friction ratio) can be not less than about 1.2:1. Alternatively, the ratio of the greater coefficient of friction value to the lesser coefficient value can be not less than about 1.4:1, and optionally can be not less than about 1.6:1. In additional aspects, a ratio of the greater coefficient of friction value to the lesser coefficient of friction value can be not more than about 3.00:1. Alternatively, the ratio of the greater coefficient of friction value to the lesser coefficient value can be not more than about 2.85:1, and optionally can be not more than about 2.70:1 to provide improved performance.

Figure 6:
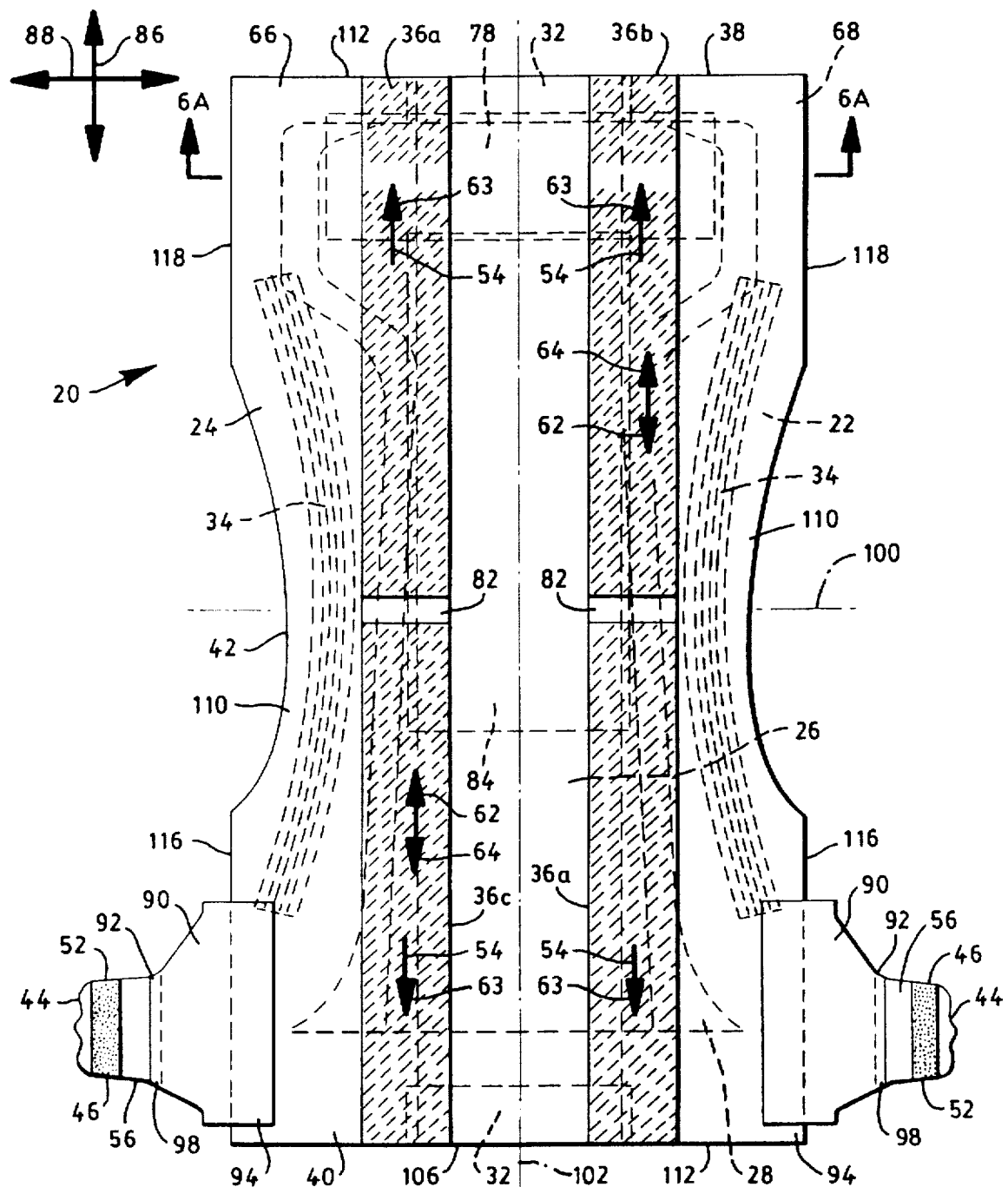
FIG. 6 representatively shows a top view of an article of the invention where a plurality of fit panel portions are located on the body-facing surfaces of a pair of containment flaps.
Figure 6A:
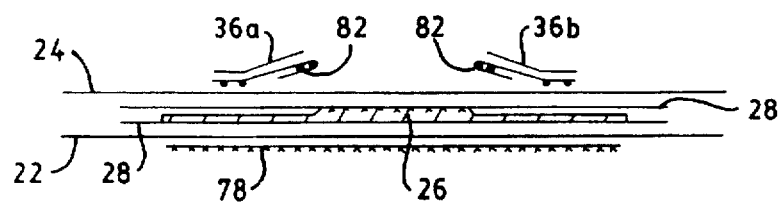
FIG. 6A representatively shows a schematic, lateral cross-sectional view of the article illustrated in FIG. 6.

With reference to FIGS. 6 and 6A, another aspect of the invention can provide a diaper article wherein the inside fit panel 36 is configured as one or more component portions of the containment flaps 82. As representatively shown, each containment flap can include one or more operationally distinct inside fit panel portions. In particular aspects, a first containment flap can have a pair of longitudinally opposed fit panel portions 36a and 36c operatively attached to provide a skin-contacting bodyside surface of the first containment flap. Similarly, a second containment flap can include one or more and operationally distinct inside fit panel portions, such as the fit panel portions 36b and 36d attached to provide a body-contacting, bodyside surface of the second containment flap. In the shown configuration, the basis line 54 of each inside fit panel portion is substantially parallel to the longitudinal direction 86. Optionally, the basis line of each fit panel portion can be arranged with a selected slant angle relative to the longitudinal direction 86, as desired.

The fit panel portions 36a and 36b desirably are relatively offset toward the front waistband section 38. With respect to these front fit panel portions, the coefficient of friction value exhibited when sliding along the fit panel in its inward basis direction is less than the coefficient of friction value exhibited when sliding in the outward basis direction. Accordingly, the maximal basis direction 63 of the fit panel portions 36a and 36b is along the relatively outward direction of their basis lines 54.

The fit panel portions 36c and 36d have a direction-dependent coefficient of friction value which is configured substantially opposite to the direction-dependent coefficient of friction value exhibited by the front fit panel portions 36a and 36b. The coefficient of friction value exhibited when sliding on the rear fit panel portions in the inward basis direction moving generally away from the rear waistband edge is less than the coefficient of friction value exhibited when sliding along the outward basis direction generally toward the longitudinally terminal, back waistband edge of the article. As a result, the maximal basis direction 63 of the fit panel portions 36c and 36d is along the relatively outward direction of their basis lines 54.

Figure 8A:
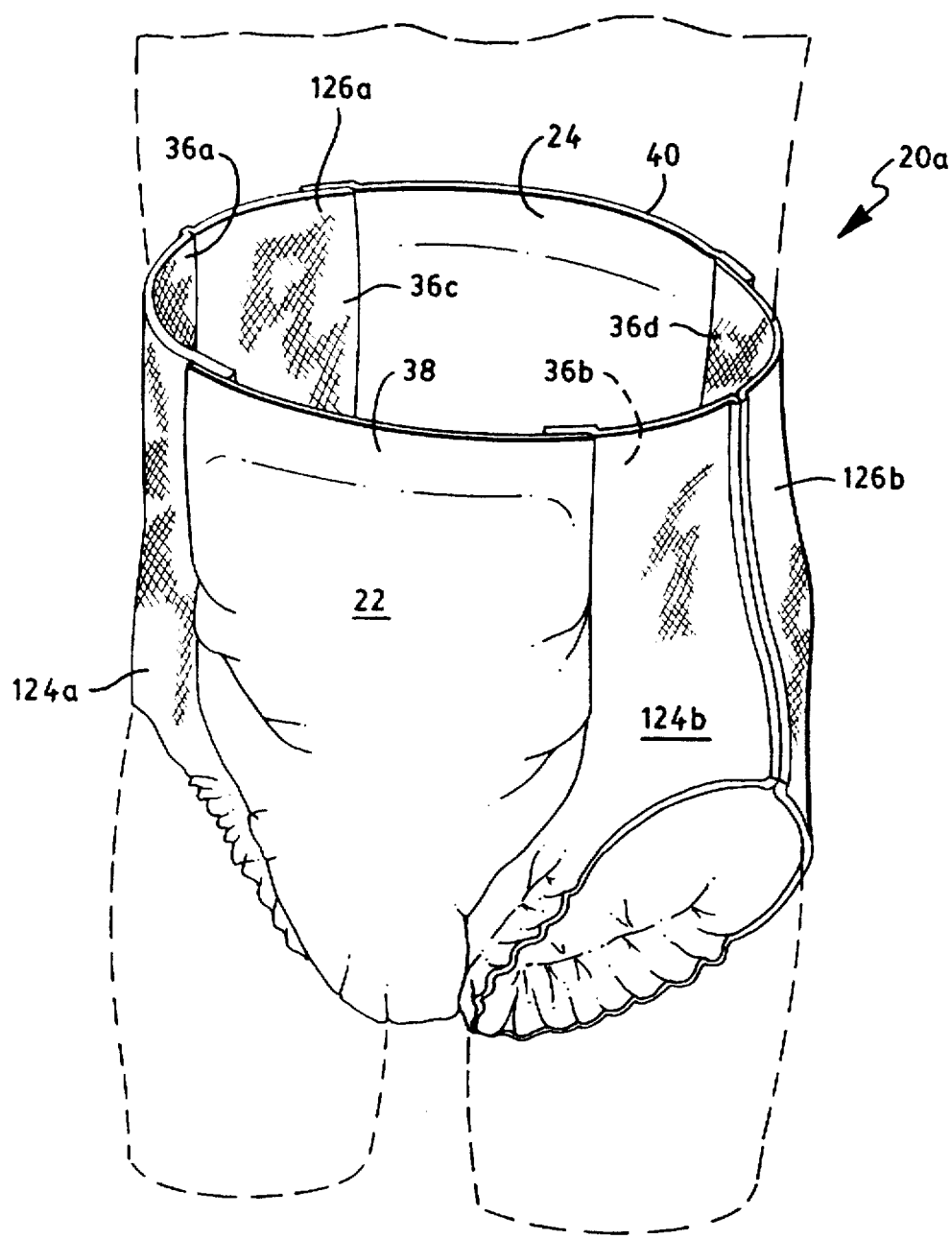
FIG. 8A representatively shows a schematic, perspective view of the article illustrated in FIG. 8.

With reference to FIGS. 8, and 8A, the present invention can provide an absorbent article 20a configured with a plurality of side members 124 and 126. The side members may or may not be elastomerically contractible and extensible, as desired. In the representatively shown arrangement, for example, a first laterally opposed pair of the side members 124 are positioned and affixed to the sides of the article at a first waistband section of the article, and a second laterally opposed pair of the side members 126 are positioned and affixed to the sides of the article at a second waistband section of the article. The illustrated arrangement is shown in a generally flat-out condition where the article is partially assembled and partially completed. With reference to FIG. 8A, the side members 124a and 124b can be joined and attached to corresponding side members 126a and 126b, respectively, along appointed side seams to form a three-dimensional training pant article. The training pant can include a liquid permeable topsheet layer 24, a substantially liquid-impermeable backsheet layer 22 and an absorbent body 26 sandwiched between the topsheet and backsheet layers. In desired constructions, the training pant can include supplemental waist and/or leg elastics, and internal containment flaps. Examples of suitable training pant configurations are described in U.S. Pat. No. 4,940,464 issued Jul. 10, 1990 to P. VanGompel et al., the entire disclosure of which is hereby incorporated by reference in a manner that is consistent herewith.

At least one, and desirably each of the side members 124 and 126 can provide for an operationally distinct, inside fit panel portion. In particular aspects, a first waistband end of the article can have the side members 124a and 124b operatively constructed and arranged to provide for a pair of laterally opposed fit panel portions 36a and 36b which are disposed on a skin-contacting bodyside surface of the side members 124a and 124b, respectively. Similarly, a second waistband end of the article can have the side members 126a and 126b operatively constructed and arranged to provide for a pair of laterally opposed fit panel portions 36c and 36d which are disposed on a skin-contacting bodyside surface of the side members 126a and 126b, respectively. In the shown configuration, the basis line 54 of each inside fit panel portion is substantially parallel to the longitudinal direction 86. Optionally, the basis line of each fit panel portion can be arranged with a selected slant angle relative to the longitudinal direction 86, as desired.

With respect to the fit panel portions 36a and 36b, the coefficient of friction value exhibited when sliding along the fit panel in its inward basis direction is less than the coefficient of friction value exhibited when sliding in the relatively outward basis direction. Accordingly, the maximal basis direction 63 of the illustrated configuration of the fit panel portions 36a and 36b is along the relatively outward direction of their basis lines 54.

The fit panel portions 36c and 36d desirably are relatively offset toward the back waistband section 40. These back fit panel portions have a direction-dependent coefficient of friction value which is configured substantially opposite to the direction-dependent coefficient of friction value exhibited by the fit panel portions 36a and 36b. The coefficient of friction value exhibited when sliding on the rear fit panel portions in the inward basis direction moving generally away from the rear waistband edge is less than the coefficient of friction value exhibited when sliding along the outward basis direction generally toward the longitudinally terminal, back waistband edge of the article. Accordingly, the maximal basis direction 63 of the illustrated configuration of fit panel portions 36a and 36b is along the relatively outward direction of their basis lines 54. When the fully assembled training pant product is worn by a child, the high coefficient of friction, maximal direction 63 extends generally upwardly toward the terminal edges which extend laterally along waistband boundary of the article.

Friction Testing Procedure

For the purposes of the present invention, a suitable technique for determining the coefficient of friction values of a material employs the following procedure. The test procedure particularly refers to the testing of a "fabric" material. It should be readily appreciated, however, that such reference is merely exemplary, and that the testing procedure can also be employed to determine the relative coefficient of friction values for the other types of materials employed to form the fit panels which are incorporated into the present invention. For such other materials, the procedure can be read by appropriately substituting the term, "fit panel material", for the term, "fabric".

The kinetic coefficient of friction values instead of the static coefficient of friction values are employed for describing the present invention. For many materials, such as the fabric materials described in the present specification, the static coefficient of friction can be greater than the kinetic coefficient of friction. For example, the difference can be about 10%–100%. While not intending to be bound by any particular theory, it is believed that the kinetic coefficient of friction values are more reproducible and are more representative of actual product use conditions. The kinetic coefficient of friction can be determined using ASTM method D 1894-93, published December 1993; with the following particulars.

Apparatus

A MONITOR/SLIP & FRICTION™ Model 32-06 test apparatus was used with a 200±5 gram COF (Coefficient Of Friction) Testing Sled and foam, part number 32-06-02; both of which are available from Testing Machines, Inc., Amityville, N.Y. 11701-2882. This apparatus is equipped with a digital display, and the apparatus can automatically calculate and display the kinetic coefficient of friction.

A contact adhesive was used to adhere foam to the sled. Suitable adhesives are available from Armstrong World, Inc., Lancaster, Pa. 17604.

A cardboard backing, approximately 0.8 to 1.5 mm thick and in the form of a 22.9 cm square, is used a disposable backing to hold the fabric on the test bed without buckling. The cardboard must be sufficiently rigid that is does not noticeably flex during testing.

Double sided attachment tape, such as ¼' (0.635 cm) wide, clear; 3M #665 was used to hold fabric strips to the sled and to the cardboard backing. Such adhesive tape is available from 3M Corporation, a business having offices in St. Paul, Minn.

Test Specimens

Test fabric is cut into the shape of a 22.9 cm square for mounting on the backing, and is cut into the shape of a 6.4 cm square for mounting on the sled.

Using double-sided attachment tape, mount the larger fabric square to the cardboard backing. Many fabrics are two sided, that is each face has different properties. When such fabrics are tested, identify the surface of interest and mount the fabric with the surface of interest facing away from the backing. The direction of maximum friction of the fabric is estimated by observing and feeling its texture and grain, such as by sliding the hand along the fabric to determine its direction of relatively greatest friction and relatively lowest friction. The fabric is mounted to the backing with the estimated maximum friction direction (high friction direction) parallel to one side edge of the backing square. The maximum or high friction direction of a material corresponds to the maximal basis direction of the material, which is the direction of sliding along which the sliding object is resisted with the largest coefficient of friction provided by the fit panel material. The situation where the sliding object is resisted with the largest coefficient of friction provided by the fit panel material can be referred to as sliding "against the grain".

Where the test fabric is provided as a plurality of narrow fabric strips, the fabric strips are taped to the backing with all of the strips aligned in the same direction. Place the fabric strips parallel to one another and as close to each other as possible without overlapping.

The fabric-against-fabric COF determination requires that half the measurements be taken with fabric attached to the sled with the high coefficient of friction direction of the fabric in the same direction as the motion of the sled; and half the measurements be taken with fabric attached to the sled with the high coefficient of friction direction of the fabric in the direction opposite to the motion of the sled. Fabrics are attached to the sled with tape. Many fabrics are two-sided, that is each major face-surface of the fabric has different properties. When such fabrics are tested, identify the surface of interest and make sure that the surface of interest is facing away from the sled when mounted.

Preparation of Apparatus

Follow the manufacture's instructions for assembling and calibrating the instrument.

Test are conducted at 0.5±0.1 ft/min.

Fabric-against-Foam Procedure

1. Place fabric mounted on backing on the test bed oriented so that the sled will slide against the grain of the fabric when the test is started. Secure the mounted fabric to the test bed.
2. Position the sled pin in the load cell mount, making sure that the sled is centered. Place the anti-skid guide over the sled.
3. Start the test by pressing the test key.
4. When the test is completed, lift the anti-skid guide and remove the sled.
5. Press enter, record the kinetic coefficient of friction.
6. Rotate the fabric sample 90° and repeat steps 1–6 until a total of eight readings are obtained.

Fabric-against-Foam Calculations

The kinetic COF is recorded for each angle of attack (direction of advance during testing), as follows:

The $1^{st}$ and $5^{th}$ values are averaged to yield result A.
The $2^{nd}$ and $6^{th}$ values are averaged to yield result B.
The $3^{rd}$ and $7^{th}$ values are averaged to yield result C.
The $4^{th}$ and $8^{th}$ values are averaged to yield result D.

The ratio of coefficient of friction is calculated between the average result value from a particular test direction and the average result value from its 180° opposite test direction. In addition, the arithmetic difference is calculated between the average result value from a particular test direction and the average result value from its 180° opposite test direction.

Fabric-against-Fabric Procedure

1. Tape the 6.4 cm fabric square to the sled so that the fabric will be pulled to slide in the direction which is against its own grain.
2. Place the 22.9 cm square fabric on the test bed oriented so that the sled will slide against the grain of the 22.9 cm square fabric when the sled is activated. Secure the 22.9 cm square fabric to the test bed.
3. Position the sled pin in the load cell mount, making sure that the sled is centered. Place the anti-skid guide over the sled.
4. Start the test by pressing the test key.
5. When the test is completed, lift the anti-skid guide and remove the sled.
6. Press enter, record the kinetic coefficient of friction.
7. Rotate the 22.9 cm square fabric sample 90° and repeat steps 2–7 until eight readings are obtained with the 6.4 cm square fabric mounted on the sled so that the 6.4 cm square fabric is pulled against its own grain.
8. Remove the 6.4 cm fabric square from the sled, rotate it 180°, and reattach to the sled. Repeat steps 2–7 until eight additional readings are obtained.

Fabric-against-Fabric Calculations

The kinetic COF is recorded for each angle of attack (direction of advance), as follows:

The $1^{st}$ and $5^{th}$ values are averaged to yield the result E.
The $2^{nd}$ and $6^{th}$ values are averaged to yield the result F.
The $3^{rd}$ and $7^{th}$ values are averaged to yield the result G.
The $4^{th}$ and $8^{th}$ values are averaged to yield the result H.
The $9^{th}$ and $13^{th}$ values are averaged to yield the result I.
The $10^{th}$ and $14^{th}$ values are averaged to yield the result J.
The $11^{th}$ and $15^{th}$ values are averaged to yield the result K.
The $12^{th}$ and $16^{th}$ values are averaged to yield the result L.

The ratio of coefficient of friction is calculated between the average result value from a particular test direction and the average result value from its 180° opposite test direction. In addition, the arithmetic difference is calculated between the average result value from a particular test direction and the average result value from its 180° opposite test direction.

Basis Line Determination

With both the fabric-against-foam and fabric-against-fabric testing procedures, the ratio of coefficient of friction is calculated between the averaged result value from a particular test direction and the averaged result value from its 180°-opposite test direction. The opposed pair of averaged result values which give the largest ratio define the basis line of the fabric. In the following Table 1, the opposed pair of result values which determine the basis line of the material is appropriately marked.

EXAMPLES

The following examples are presented to provide a more detailed understanding of the invention, and are not intended to limit the scope of the invention. It should be noted that Examples 1–8 employed the fabric-against-foam test procedure, and that Examples 9–11 employed the fabric-against-fabric test procedure.

Example 1

Strips of 0.5 inch wide 3M Microhook material (XMH-4130, CS-200, 5220P2b001-OP) were applied to a 22.9 cm square cardboard backing with the strips placed parallel, as close as possible without overlapping, all with the grain oriented in the same direction. (The microhook material has a plastic film substrate with plastic hooks protruding about 0.7 mm from the surface. Most commonly microhook is used as part of a mechanical fastener system.) This microhook material was tested for coefficient of friction, and had the appropriate differential friction properties to be an acceptable fit panel material. The properties of the material of this example are summarized in Table 1.

Example 2

This example evaluated a Gilford brand style 57105, color: 46H1, forest green color, an elastic velvet with approximately 0.8 mm fibers protruding from the surface. The velvet had a well defined grain. This fabric was tested to determine its coefficient of friction properties, and had the appropriate differential friction properties to be an acceptable fit panel material. The properties of the material of this example are summarized in Table 1.

Example 3

A white elastic velvet fabric with approximately 0.8 mm surface fibers was tested to determine its coefficient of friction properties, and had the appropriate differential friction properties to be an acceptable fit panel material. The properties of the material of this example are summarized in Table 1.

Example 4

A red non-elastic velvet with 0.8 mm surface fibers was tested to determine its coefficient of friction properties, and had the appropriate differential friction properties to be an acceptable fit panel material. The properties of the material of this example are summarized in Table 1.

Example 5

Black "fake fur" has oriented surface fibers of approximately 10 mm length was tested to determine its coefficient of friction properties, and had the appropriate differential friction properties to be an acceptable fit panel material. The properties of the material of this example are summarized in Table 1.

Example 6

The flocked foam of this example had a fuzzy surface, with fibers projecting approximately 1.2 mm. The surface fibers are isotropic, unlike velvet. This fabric did not have the appropriate differential friction properties to be an acceptable fit panel material. The properties of the material of this example are summarized in Table 1.

Example 7

The sample NBL (Neck Bonded Laminate) material of this example corresponded to the elasticized, stretch side panel material found in commercially available HUGGIES® Supreme disposable diapers. The NBL material was not velvet-like, and did not exhibit suitable direction-dependent coefficient of friction properties. The NBL material had few fibers projecting from its surface, and did not have the appropriate differential friction properties to be an acceptable fit panel material. The properties of the material of this example are summarized in Table 1.

Example 8

The crushed velvet of this example had approximately 0.9 mm long surface fibers. The fabric had alternating bands of material with grain in opposite directions, and did not have the appropriate differential friction properties to be an acceptable fit panel material. The properties of the material of this example are summarized in Table 1.

Example 9

The blue upholstery fabric of this example was a velvet with strongly oriented fibers, approximately 1.4 mm long. This fabric has curved surface fibers, and had the appropriate differential friction properties to be an acceptable fit panel material. The properties of the material of this example are summarized in Table 1.

Example 10

The royal blue velvet of this example was style 30083 from Charbert Division of NFA, 299 Church Street, Alton, R.I. 02894. According to the label, this material had the following properties: composed of 88% nylon and 13% spandex; basis weight of 6.9 osy (234 g/m$^2$); stretchability along its length of 300%; stretchability along its width of 145%. It was a ribbed, elastic, velvet fabric with oriented surface fibers approximately 1.0 mm long. It had the appropriate differential friction properties to be an acceptable fit panel material, and the properties of the material of this example are summarized in Table 1.

Example 11

The teal velvet of this example was Baras style 72003. It had approximately 1.2 mm long surface fibers on a non-stretchy backing, and had the appropriate differential friction properties for an acceptable fit panel material. The properties of the material of this example are summarized in Table 1.

TABLE 1

| | Coefficient of Friction Values and Calculations | | | | |
|---|---|---|---|---|---|
| Example | Direction of Advance; Result type | COF value | Average COF for each type of Result | Ratio of opposed, avg. Result values | Difference between opposed, avg. Result values |
| 1 | A | 0.892 | | | |
| | A | 0.835 | 0.86 | 0.75:1.00 A:C | −0.29 A–C |
| | B | 0.947 | | | |
| | B | 0.986 | 0.97 | 0.94:1.00 B:D | −0.06 B–D |
| | C | 0.998 | | | |
| | C | 1.304 | 1.15 | 1.33:1.00 C:A | 0.29 C–A* |
| | D | 1.032 | | | |
| | D | 1.014 | 1.02 | 1.06:1.00 D:B | 0.06 D–B |
| 2 | A | 2.067 | | | |
| | A | 2.029 | 2.05 | 1.20:1.00 A:C | 0.34 A–C* |
| | B | 2.111 | | | |
| | B | 2.111 | 2.11 | 1.08:1.00 B:D | 0.15 B–D |
| | C | 1.694 | | | |
| | C | 1.730 | 1.71 | 0.84:1.00 C:A | −0.34 C–A |
| | D | 1.963 | | | |
| | D | 1.957 | 1.96 | 0.93:1.00 D:B | −0.15 D–B |
| 3 | A | 1.640 | | | |
| | A | 1.627 | 1.63 | 1.20:1.00 A:C | 0.27 A–C* |
| | B | 1.324 | | | |
| | B | 1.388 | 1.36 | 0.87:1.00 B:D | −0.20 B–D |
| | C | 1.330 | | | |
| | C | 1.396 | 1.36 | 0.83:1.00 C:A | −0.27 C–A |
| | D | 1.588 | | | |
| | D | 1.524 | 1.56 | 1.15:1.00 D:B | 0.20 D–B |
| 4 | A | 1.409 | | | |
| | A | 1.446 | 1.43 | 1.17:1.00 A:C | 0.21 A–C* |
| | B | 1.428 | | | |
| | B | 1.494 | 1.46 | 1.12:1.00 B:D | 0.15 B–D |
| | C | 1.284 | | | |
| | C | 1.157 | 1.22 | 0.85:1.00 C:A | −0.21 C–A |
| | D | 1.278 | | | |
| | D | 1.340 | 1.31 | 0.90:1.00 D:B | −0.15 D–B |
| 5 | A | 1.120 | | | |
| | A | 1.136 | 1.13 | 1.10:1.00 A:C | 0.10 A–C |
| | B | 1.174 | | | |
| | B | 1.251 | 1.21 | 1.14:1.00 B:D | 0.14 B–D* |
| | C | 1.081 | | | |
| | C | 0.977 | 1.03 | 0.91:1.00 C:A | −0.10 C–A |
| | D | 1.098 | | | |
| | D | 1.038 | 1.07 | 0.88:1.00 D:B | −0.14 D–B |
| 6 | A | 1.585 | | | |
| | A | 1.605 | 1.60 | 1.09:1.00 A:C | 0.13 A–C |
| | B | 1.666 | | | |
| | B | 1.621 | 1.64 | 1.11:1.00 B:D | 0.16 B–D* |
| | C | 1.476 | | | |
| | C | 1.458 | 1.47 | 0.92:1.00 C:A | −0.13 C–A |
| | D | 1.465 | | | |
| | D | 1.505 | 1.49 | 0.90:1.00 D:B | −0.16 D–B |
| 7 | A | 1.043 | | | |
| | A | 1.070 | 1.06 | 0.98:1.00 A:C | −0.02 A–C |
| | B | 0.988 | | | |
| | B | 1.126 | 1.06 | 0.93:1.00 B:D | −0.08 B–D |
| | C | 1.090 | | | |
| | C | 1.071 | 1.08 | 1.02:1.00 C:A | 0.02 C–A |
| | D | 1.128 | | | |
| | D | 1.138 | 1.13 | 1.07:1.00 D:B | 0.08 D–B* |

TABLE 1-continued

Coefficient of Friction Values and Calculations

| Example | Direction of Advance; Result type | COF value | Average COF for each type of Result | Ratio of opposed, avg. Result values | Difference between opposed, avg. Result values |
|---|---|---|---|---|---|
| 8 | A | 1.730 | | | |
|   | A | 1.743 | 1.74 | 1.01:1.00 A:C | 0.02 A-C |
|   | B | 1.728 | | | |
|   | B | 1.592 | 1.66 | 0.99:1.00 B:D | −0.02 B-D |
|   | C | 1.777 | | | |
|   | C | 1.666 | 1.72 | 0.99:1.00 C:A | −0.02 C-A |
|   | D | 1.668 | | | |
|   | D | 1.695 | 1.68 | 1.01:1.00 D:B | 0.02 D-B* |
| 9 | E | 1.740 | | | |
|   | E | 1.894 | 1.82 | 2.48:1.00 E:K | 1.09 E-K* |
|   | F | 1.479 | | | |
|   | F | 1.548 | 1.51 | 1.87:1.00 F:L | 0.70 F-L |
|   | G | 1.147 | | | |
|   | G | 1.167 | 1.16 | 1.16:1.00 G:I | 0.16 G-I |
|   | H | 1.789 | | | |
|   | H | 1.794 | 1.79 | 2.13:1.00 H:J | 0.95 H-J |
|   | I | 0.995 | | | |
|   | I | 1.002 | 1.00 | 0.86:1.00 I:G | −0.16 I-G |
|   | J | 0.830 | | | |
|   | J | 0.849 | 0.84 | 0.47:1.00 J:H | −0.95 J-H |
|   | K | 0.727 | | | |
|   | K | 0.737 | 0.73 | 0.40:1.00 K:E | −1.09 K-E |
|   | L | 0.787 | | | |
|   | L | 0.832 | 0.81 | 0.53:1.00 L:F | −0.70 L-F |
| 10 | E | 1.445 | | | |
|    | E | 1.475 | 1.46 | 1.95:1.00 E:K | 0.71 E-K* |
|    | F | 1.022 | | | |
|    | F | 1.257 | 1.14 | 1.52:1.00 F:L | 0.39 F-L |
|    | G | 0.850 | | | |
|    | G | 0.892 | 0.87 | 1.07:1.00 G:I | 0.06 G-I |
|    | H | 1.365 | | | |
|    | H | 1.381 | 1.37 | 1.72:1.00 H:J | 0.58 H-J |
|    | I | 0.810 | | | |
|    | I | 0.811 | 0.81 | 0.93:1.00 I:G | −0.06 I-G |
|    | J | 0.772 | | | |
|    | J | 0.823 | 0.80 | 0.58:1.00 J:H | −0.58 J-H |
|    | K | 0.730 | | | |
|    | K | 0.767 | 0.75 | 0.51:1.00 K:E | −0.71 K-E |
|    | L | 0.750 | | | |
|    | L | 0.750 | 0.75 | 0.66:1.00 L:F | −0.39 L-F |
| 11 | E | 1.537 | | | |
|    | E | 1.605 | 1.57 | 1.74:1.00 E:K | 0.67 E-K* |
|    | F | 1.392 | | | |
|    | F | 1.429 | 1.41 | 1.35:1.00 F:L | 0.37 F-L |
|    | G | 1.213 | | | |
|    | G | 1.221 | 1.22 | 0.85:1.00 G:I | −0.21 G-I |
|    | H | 1.098 | | | |
|    | H | 1.178 | 1.14 | 1.04:1.00 H:J | 0.04 H-J |
|    | I | 1.427 | | | |
|    | I | 1.435 | 1.43 | 1.18:1.00 I:G | 0.21 I-G |
|    | J | 1.070 | | | |
|    | J | 1.123 | 1.10 | 0.96:1.00 J:H | −0.04 J-H |
|    | K | 0.899 | | | |
|    | K | 0.902 | 0.90 | 0.57:1.00 K:E | −0.67 K-E |
|    | L | 1.030 | | | |
|    | L | 1.058 | 1.04 | 0.74:1.00 L:F | −0.37 L-F |

Example 12

Figure 7:
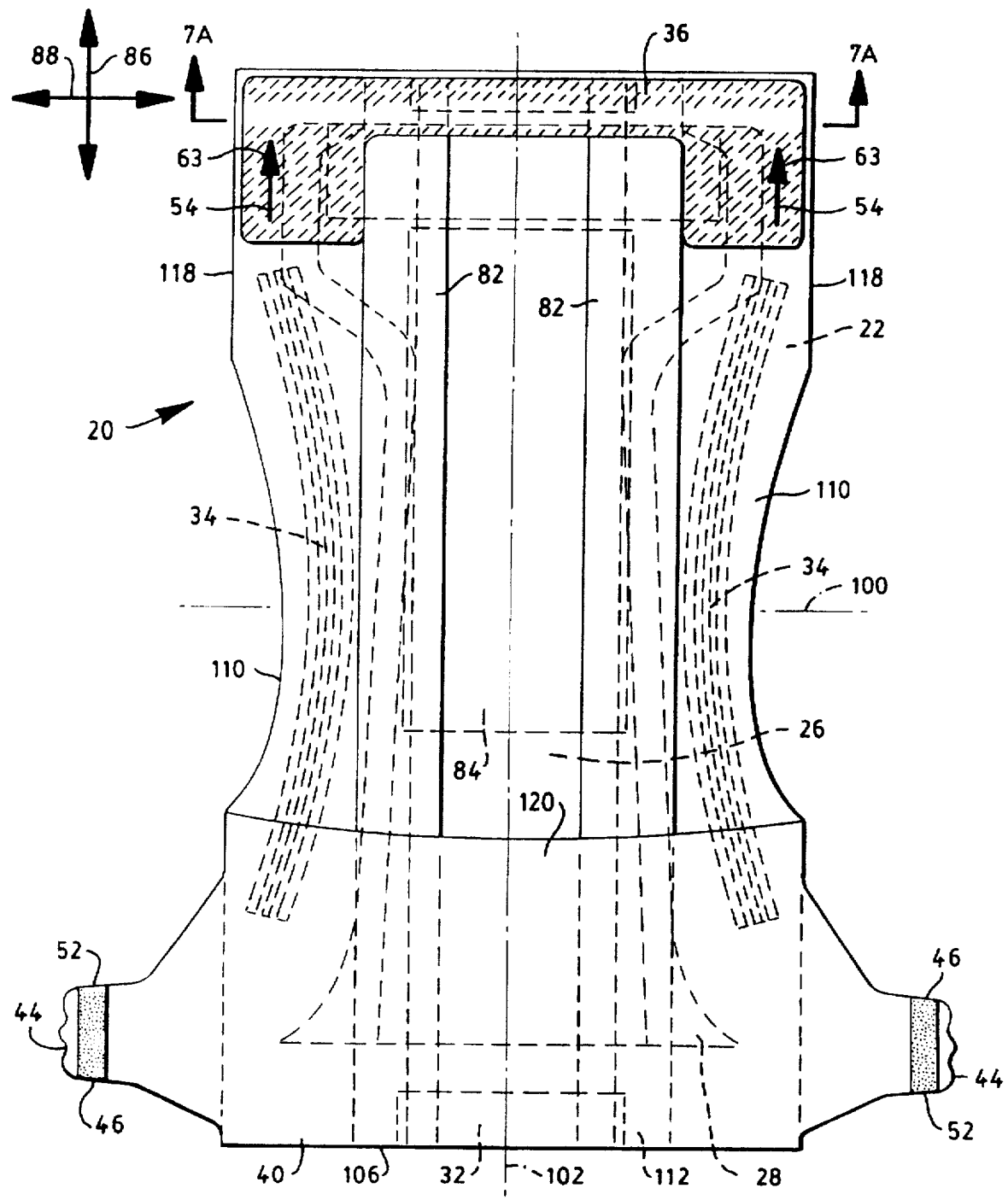
FIG. 7 representatively shows a top view of an article of the invention having a waist flap member and a shaped, contoured fit panel positioned on the bodyside surface of the article.
Figure 7A:
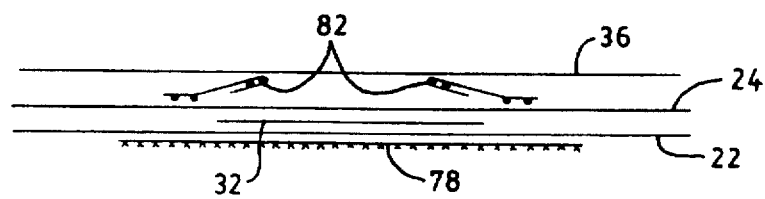
FIG. 7A representatively shows a schematic, lateral cross-sectional view of the article illustrated in FIG. 7.

Four medium size diapers were prepared with the elasticized band or waistband member 120 positioned across the inside surface of the back of the diaper, extending substantially from fastener tab to fastener tab, as representatively shown in FIGS. 7 and 7A. These diapers, however, did not include fit panels, and were designated as the "control" product.

Four test diapers were prepared with the elasticized band or waistband member 120 positioned across the inside surface of the back of the diaper, extending substantially from fastener tab to fastener tab. In addition, the test diapers included a fit panel affixed at the inner, bodyside surface of the diaper front waistband section. The fit panel had the U-shaped configuration illustrated in FIG. 7, and was composed of the blue upholstery fabric described in Example 9. The grain of the fabric provided a basis line which was aligned substantially along the diaper longitudinal direction 86, and the maximal basis direction was pointed away from the crotch of the diaper and toward the border edges of the diaper.

Four children wore each of the two diaper types described above. All of the children were ambulatory, and weighed between 11 kg and 14 kg. A reference mark was made on each child's abdomen, and the amount of diaper movement was evaluated with respect to the reference mark. After approximately 100 grams of saline were added to each of the diapers, the children were allowed to walk around and play for 30 minutes before evaluation. Photographs of the diapers were taken to record front panel slippage. The degree of slippage was ranked on a 1 (least slippage) to 4 (most slippage) scale. The results were as follows:

| | front diaper slippage (1 = least, 4 = most) diaper code | |
|---|---|---|
| Subject | control | front fit panel |
| Jo | 4 | 1 |
| Da | 1 | 2 |
| Tr | 3 | 1 |
| Ky | 3 | 1 |
| mean | 2.75 | 1.25 |

This experiment demonstrated that the diapers of the invention were able to stay in place better than the control diapers, which lacked fit panels with differential friction.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An article having a front waistband section, a back waistband section, an intermediate section interconnecting said front and back waistband sections, a longitudinal direction, a cross-direction and a laterally extending line which is longitudinally centered in said article, said article comprising:

at least a first fit panel connected to an inside surface of at least one of said waistband sections, said fit panel having a direction-dependent coefficient of friction value along a basis line of said fit panel, wherein a first coefficient of friction value is exhibited when sliding on said fit panel along said basis line in a first inward direction generally toward said laterally extending line, a second, different coefficient of friction value is exhibited when sliding on said fit panel along said basis line in a second outward direction opposite said first direction, said first and second coefficient of friction values are determined with respect to testing against foam, and the greater of said first and second coefficient of friction values is not more than about 2.4.

2. An article as recited in claim 1, wherein said first coefficient of friction value is less than said second coefficient of friction value.

3. An article as recited in claim 1, wherein said first coefficient of friction value is greater than said second coefficient of friction value.

4. An article as recited in claim 1, further comprising:
   a backsheet layer;
   a liquid permeable topsheet layer connected in superposed relation to said backsheet layer; and
   an absorbent body sandwiched between said backsheet layer and topsheet layer.

5. An article as recited in claim 1, further comprising:
   a backsheet layer;
   a liquid permeable topsheet layer connected in superposed relation to said backsheet layer;
   an absorbent body sandwiched between said backsheet layer and topsheet layer; and
   at least one fastener affixed to at least one of said waistband sections for securing said waistband sections about a wearer.

6. An article as recited in claim 1, wherein the greater of said first and second coefficient of friction values is not less than about 1.0.

7. An article as recited in claim 1, wherein the lesser of said first and second coefficient of friction values is not less than about 0.6.

8. An article as recited in claim 1, wherein the lesser of said first and second coefficient of friction values is not greater than about 1.9.

9. An article as recited in claim 1, wherein the lesser of said first and second coefficient of friction values subtracted from the greater of the values is not less than about 0.15.

10. An article as recited in claim 1, wherein the lesser of said first and second coefficient of friction values subtracted from the greater of the values is not more than about 1.50.

11. An article as recited in claim 1, wherein a ratio of the greater of said first and second coefficient of friction values to the lesser of the values is not less than about 1.15:1.

12. An article as recited in claim 1, wherein a ratio of the greater of said first and second coefficient of friction values to the lesser of the values is not more than about 3.00:1.

13. An article as recited in claim 1, further comprising an elasticizing means for providing an elastomeric stretchability to said fit panel along said cross-direction of said article.

14. An article as recited in claim 1, wherein said fit panel comprises a fabric having a directional grain substantially along said basis line.

15. An article as recited in claim 1, wherein said fit panel comprises a fabric having a majority of its fibers configured with a directed orientation along a fabric grain which is substantially along said basis line.

16. An article as recited in claim 13, wherein said fit panel comprises a nonwoven fabric.

17. An article as recited in claim 13, wherein said fit panel comprises a velvet fabric.

18. An article as recited in claim 1, wherein said fit panel comprises a film material having a substrate with projecting elements extending from a surface of said substrate, said material having a directional grain aligned substantially along said basis line.

19. An article as recited in claim 1, wherein said at least one waistband section has opposed, laterally extending ear portions, and each ear portion has a region of said fit panel attached to a bodyside surface of the ear portion.

20. An article as recited in claim 1, wherein said fit panel is a separate member assembled into said article.

21. An article as recited in claim 1, wherein said fit panel is a separately provided member which is assembled into said article and arranged to overlie a bodyside surface of said topsheet layer.

22. An article as recited in claim 1, wherein said fit panel is a separately provided member assembled into said article and configured to provide a waist containment flap having a laterally extending fixed edge portion, and a laterally extending movable edge portion located inboard from said fixed edge portion.

23. An article as recited in claim 1, wherein said fit panel is integrally formed with said topsheet layer.

24. An article as recited in claim 1, wherein at least one said fit panel is connected to an inside surface of each of said front and back waistband sections.

25. An article as recited in claim 1, wherein said basis line is arranged to slant at a laterally outward angle which is not less than about 15 degrees.

26. An article as recited in claim 1, wherein said basis line is arranged to slant at a laterally outward angle which is not more than about 85 degrees, relative to the longitudinal direction of said article.

27. An article as recited in claim 1, wherein said basis line is arranged to slant at a laterally outward angle which is not more than about 60 degrees, relative to said longitudinal direction of said article.

28. An article as recited in claim 1, further comprising:
   at least a supplemental fit panel connected to an outside surface of a second of said waistband sections, said supplemental fit panel appointed for contacting and interacting with said first fit panel when said article is placed in use and having a direction-dependent coefficient of friction value along a basis line of said supplemental fit panel with a first supplemental coefficient of friction value which is different than a second supplemental coefficient of friction value, said first supplemental coefficient of friction value exhibited when sliding on said supplemental fit panel along said basis line in a first inward direction generally toward said lateral line and said second supplemental coefficient of friction value exhibited when sliding on said supplemental fit panel along said basis line in a second outward direction which is opposite said first direction.

29. An article as recited in claim 24, wherein said first supplemental coefficient of friction value is less than said second supplemental coefficient of friction value.

30. An article as recited in claim 24, wherein said first supplemental coefficient of friction value is greater than said second supplemental coefficient of friction value.

31. An article as recited in claim 1, wherein said fit panel is configured to operably reduce a drooping of said article when said article is worn.

32. An article as recited in claim 1, wherein said fit panel is located at said front waistband section of said article.

33. An article as recited in claim 1, wherein said fit panel is located at said back waistband section of said article.

34. An article as recited in claim 29, wherein said supplemental fit panel is located at said back waistband section of said article.

35. An article as recited in claim 30, wherein said supplemental fit panel is located at said front waistband section of said article.

36. An article as recited in claim 31, wherein said back waistband section has a pair of opposed, laterally extending back ear portions, and each back ear portion has a region of said supplemental fit panel attached to a bodyside surface of the back ear portion.

37. An article as recited in claim 32, wherein said front waistband section has a pair of opposed, laterally extending front ear portions, and each front ear portion has a region of said supplemental fit panel attached to an outerside surface of the front ear portion.

38. An article as recited in claim 1, wherein said article includes a pair of elasticized, longitudinally extending containment flaps located on opposite sides of a longitudinally extending centerline of said article, and wherein said fit panel includes a plurality of individual, spatially separated fit panel portions, each fit panel portion connected to provide a bodyside surface of at least a portion of a one of said containment flaps.

* * * * *